United States Patent
Horikoshi et al.

(10) Patent No.: US 9,675,075 B2
(45) Date of Patent: Jun. 13, 2017

(54) PEST CONTROL COMPOSITION

(71) Applicant: MEIJI SEIKA PHARMA CO., LTD., Tokyo-to (JP)

(72) Inventors: Ryo Horikoshi, Kanagawa-ken (JP); Kazuhiko Oyama, Kanagawa-ken (JP); Mitsuyuki Yabuzaki, Shizuoka-Ken (JP)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/471,393

(22) Filed: Aug. 28, 2014

(65) Prior Publication Data
US 2014/0371178 A1  Dec. 18, 2014

Related U.S. Application Data

(62) Division of application No. 12/450,018, filed as application No. PCT/JP2008/054316 on Mar. 10, 2008, now Pat. No. 8,859,462.

(30) Foreign Application Priority Data

Mar. 8, 2007 (JP) ................................ 2007-058540

(51) Int. Cl.
| | |
|---|---|
| A01N 47/40 | (2006.01) |
| A01N 43/88 | (2006.01) |
| A01N 43/66 | (2006.01) |
| A01N 43/56 | (2006.01) |
| A01N 43/40 | (2006.01) |
| A01N 43/36 | (2006.01) |
| A01N 43/08 | (2006.01) |
| A01N 43/90 | (2006.01) |
| A01N 53/00 | (2006.01) |

(52) U.S. Cl.
CPC ............ *A01N 47/40* (2013.01); *A01N 43/08* (2013.01); *A01N 43/36* (2013.01); *A01N 43/40* (2013.01); *A01N 43/56* (2013.01); *A01N 43/66* (2013.01); *A01N 43/88* (2013.01); *A01N 43/90* (2013.01); *A01N 53/00* (2013.01)

(58) Field of Classification Search
CPC ........ A01N 47/40; A01N 43/36; A01N 43/40; A01N 43/88; A01N 43/66; A01N 43/56; A01N 43/08; A01N 43/90; A01N 53/00
See application file for complete search history.

(56) References Cited

U.S. PATENT DOCUMENTS

| | | |
|---|---|---|
| 5,807,721 A | 9/1998 | Omura et al. |
| 2006/0013564 A1 | 1/2006 | Hamada et al. |
| 2006/0281780 A1 | 12/2006 | Goto et al. |
| 2007/0203181 A1 | 8/2007 | Yamamoto et al. |

FOREIGN PATENT DOCUMENTS

| | | |
|---|---|---|
| EP | 1 889 540 | 2/2008 |
| JP | 2993767 | 10/1999 |
| JP | 2006-513233 | 4/2006 |
| WO | 2004/060065 | 7/2004 |
| WO | 2006/013896 | 2/2006 |
| WO | 2006/129714 | 12/2006 |

OTHER PUBLICATIONS

International Search Report issued Apr. 15, 2008 in International (PCT) Application No. PCT/JP2008/054316.
H. Wang et al., "Aflavinines and Other Antiinsectan Metabolites from the Ascostromata of *Eupenicillium crustaceum* and Related Species", Applied and Environmental Microbiology, vol. 61, No. 12, pp. 4429-4435, Dec. 1995.
English translation of International Preliminary Report on Patentability and Written Opinion dated Sep. 29, 2009.
Extended European Search Report issued Sep. 27, 2011 in corresponding International Application No. EP 08 72 1732.
Japanese Office Action issued Apr. 19, 2013 in corresponding Japanese Application No. 2009-502640.

*Primary Examiner* — Sue Liu
*Assistant Examiner* — Andriae M Holt
(74) *Attorney, Agent, or Firm* — Wenderoth, Lind & Ponack, L.L.P.

(57) ABSTRACT

Disclosed is a pest control composition comprising at least one pyripyropene derivative of formula (I) or agriculturally and horticulturally acceptable salt thereof and at least one other pest control agent as active ingredients. The combined use of the two ingredients can provide a better insecticidal effect.

[Chemical formula 1]

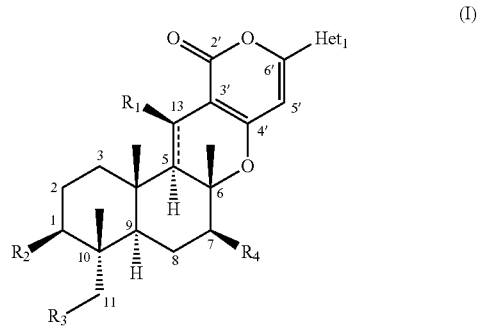

11 Claims, No Drawings

PEST CONTROL COMPOSITION

CROSS-REFERENCE TO RELATED APPLICATION

The application is based upon and claims the benefit of priority from the prior Japanese Patent Application No. 58540/2007, filed on Mar. 8, 2007; the entire contents of which are incorporated herein by reference.

BACKGROUND OF THE INVENTION

Field of Invention

The present invention relates to a pest control composition that comprises a pyripyropene derivative or an agriculturally and horticulturally acceptable salt thereof and other pest control agent and that is agriculturally and horticulturally useful.

Background Art

*Applied and Environmental Microbiology* (1995), 61(12), 4429-35 and WO 2004/060065 describe insecticidal activity of pyripyropene A, and WO 2006/129714 describes pyripyropene A derivatives and the insecticidal activity of the pyripyropene A derivatives. The Pesticide Manual, the 13th edition, published by The British Crop Protection Council and SHIBUYA INDEX, the 10th edition, 2005, published by SHIBUYA INDEX RESEARCH GROUP describe many pest control agents that have hitherto been developed and used. Up to now, however, there is no document describing the effect of a mixture of the pyripyropene derivative with other pest control agent(s).

On the other hand, control at a low dose is desired from the viewpoints of environmental consideration and influence on organisms that are not target.

SUMMARY OF THE INVENTION

The present inventors have now found a composition that comprises a pyripyropene derivative or an agriculturally and horticulturally acceptable salts thereof and other pest control agent and possesses an excellent control effect, and use of the composition. The present invention has been made based on such finding.

Accordingly, an object of the present invention is to provide a composition that comprises a pyripyropene derivative or an agriculturally and horticulturally acceptable salts thereof and other pest control agent and possesses an excellent control effect, and use of the composition.

According to one aspect of the present invention, there is provided a pest control composition comprising at least one pyripyropene derivative of formula (I) or agriculturally and horticulturally acceptable salt thereof and at least one other pest control agent as active ingredients:

[Chemical formula 1]

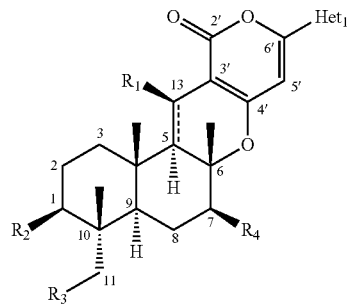

(I)

wherein
$Het_1$ represents optionally substituted 3-pyridyl,
$R_1$ represents hydroxyl,
  optionally substituted $C_{1-6}$ alkylcarbonyloxy,
  optionally substituted $C_{2-6}$ alkenylcarbonyloxy,
  optionally substituted $C_{2-6}$ alkynylcarbonyloxy,
  optionally substituted $C_{1-6}$ alkyloxy,
  optionally substituted $C_{2-6}$ alkenyloxy,
  optionally substituted $C_{2-6}$ alkynyloxy,
  optionally substituted benzyloxy, or
  oxo in the absence of a hydrogen atom at the 13-position or
the bond between 5-position and 13-position represents a double bond in the absence of $R_1$ and a hydrogen atom at the 5-position,
$R_2$ represents hydroxyl,
  optionally substituted $C_{1-18}$ alkylcarbonyloxy,
  optionally substituted $C_{2-6}$ alkenylcarbonyloxy,
  optionally substituted $C_{2-6}$ alkynylcarbonyloxy,
  optionally substituted benzoyloxy, or
  optionally substituted $C_{1-6}$ alkylsulfonyloxy,
$R_3$ represents a hydrogen atom,
  hydroxyl,
  optionally substituted $C_{1-18}$ alkylcarbonyloxy,
  optionally substituted $C_{2-6}$ alkenylcarbonyloxy,
  optionally substituted $C_{2-6}$ alkynylcarbonyloxy,
  optionally substituted benzoyloxy,
  optionally substituted $C_{1-6}$ alkylsulfonyloxy,
  optionally substituted benzenesulfonyloxy, or
  optionally substituted five- or six-membered heterocyclic thiocarbonyloxy, or
$R_2$ and $R_3$ together represent —O—$CR_2'R_3'$—O— wherein
$R_2'$ and $R_3'$, which may be the same or different, represent a hydrogen atom, $C_{1-6}$ alkyl, $C_{1-6}$ alkyloxy, $C_{2-6}$ alkenyl, optionally substituted phenyl, or optionally substituted benzyl, or $R_2'$ and $R_3'$ together represent oxo or $C_{2-6}$ alkylene, and
$R_4$ represents a hydrogen atom,
  hydroxyl,
  optionally substituted $C_{1-18}$ alkylcarbonyloxy,
  optionally substituted $C_{2-6}$ alkenylcarbonyloxy,
  optionally substituted $C_{2-6}$ alkynylcarbonyloxy,
  optionally substituted benzoyloxy,
  optionally substituted $C_{1-6}$ alkylsulfonyloxy,
  optionally substituted benzenesulfonyloxy,
  optionally substituted benzyloxy,
  optionally substituted $C_{1-6}$ alkyloxy,
  optionally substituted $C_{2-6}$ alkenyloxy,
  optionally substituted $C_{2-6}$ alkynyloxy, $C_{1-6}$ alkyloxy-$C_{1-6}$ alkyloxy, $C_{1-6}$ alkylthio-$C_{1-6}$ alkyloxy, $C_{1-6}$ alkyloxy-$C_{1-6}$ alkyloxy-$C_{1-6}$ alkyloxy, optionally substituted $C_{1-6}$ alkyloxycarbonyloxy, optionally substituted $C_{1-6}$ alkylaminocarbonyloxy, optionally substituted saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, optionally substituted saturated or unsaturated five- or six-membered heterocyclic thiocarbonyloxy, or oxo in the absence of a hydrogen atom at the 7-position.

According to a second aspect of the present invention, there is provided a method for protecting useful plants from pests, comprising treating an object pest, an object useful plant, or a seed, a soil, or a cultivation carrier of the object useful plant with the pest control composition.

There is also provided use of the above pest control composition for the protection of useful plants from pests.

DETAILED DESCRIPTION OF THE INVENTION

The term "halogen" as used herein means fluorine, chlorine, bromine, or iodine, preferably fluorine, chlorine, or bromine.

The terms "alkyl," "alkenyl," and "alkynyl" as used herein as a group or a part of a group respectively mean alkyl, alkenyl, and alkynyl that the group is of a straight chain, branched chain, or cyclic type or a type of a combination thereof unless otherwise specified. Further, for example, "$C_{1-6}$" in "$C_{1-6}$ alkyl" as a group or a part of a group means that the number of carbon atoms in the alkyl group is 1 to 6. Further, in the case of cyclic alkyl, the number of carbon atoms is at least three.

The term "heterocyclic ring" as used herein means a heterocyclic ring containing one or more, preferably one to four, heteroatoms, which may be the same or different, selected from the group consisting of nitrogen, oxygen, and sulfur atoms. Further, the expression "optionally substituted" alkyl as used herein means that one or more hydrogen atoms on the alkyl group may be substituted by one or more substituents which may be the same or different. It will be apparent to a person having ordinary skill in the art that the maximum number of substituents may be determined depending upon the number of substitutable hydrogen atoms on the alkyl group. This is true of functional groups other than the alkyl group.

3-Pyridyl represented by $Het_1$ is optionally substituted, and substituents include halogen atoms, $C_{1-4}$ alkyl, $C_{1-4}$ alkyloxy, nitro, cyano, formyl, trifluoromethyl, trifluoromethyloxy, trifluoromethylthio, trifluoromethylsulfinyl, trifluoromethylsulfonyl, acetyl, or acetyloxy. Preferred are halogen atoms and trifluoromethyl. A chlorine atom and trifluoromethyl are more preferred.

"$C_{1-6}$ alkylcarbonyloxy" represented by $R_1$ is optionally substituted, and substituents include halogen atoms, cyano, phenyl, trifluoromethyloxy, or trifluoromethylthio.

"$C_{1-18}$ alkylcarbonyloxy" represented by $R_2$, $R_3$ and $R_4$ is preferably $C_{1-6}$ alkylcarbonyloxy, more preferably ethylcarbonyloxy or $C_{3-6}$ cyclic alkylcarbonyloxy. The $C_{1-18}$ alkylcarbonyloxy group is optionally substituted, and substituents include halogen atoms, cyano, $C_{3-6}$ cycloalkyl, phenyl, trifluoromethyloxy, trifluoromethylthio, pyridyl, or pyridylthio. More preferred are halogen atoms, $C_{3-6}$ cycloalkyl, and pyridyl.

"$C_{2-6}$ alkenylcarbonyloxy" represented by $R_1$, $R_2$, $R_3$ and $R_4$ is optionally substituted, and substituents include halogen atoms, cyano, phenyl, trifluoromethyloxy, or trifluoromethylthio.

"$C_{2-6}$ alkynylcarbonyloxy" represented by $R_1$, $R_2$, $R_3$ and $R_4$ is optionally substituted, and substituents include halogen atoms, cyano, phenyl, trifluoromethyloxy, or trifluoromethylthio.

"$C_{1-5}$ alkyloxy" represented by $R_1$ and $R_4$ is optionally substituted, and substituents include halogen atoms; cyano; phenyl; trifluoromethyloxy; trifluoromethylthio; $C_{1-6}$ alkylcarbonyl optionally substituted by a halogen atom; or $C_{1-6}$ alkylcarbonyloxy optionally substituted by a halogen atom.

"$C_{2-6}$ alkenyloxy" represented by $R_1$ and $R_4$ is optionally substituted, and substituents include halogen atoms; cyano; phenyl; trifluoromethyloxy; trifluoromethylthio; $C_{1-6}$ alkylcarbonyl optionally substituted by a halogen atom; or $C_{1-6}$ alkylcarbonyloxy optionally substituted by a halogen atom.

"$C_{2-6}$ alkynyloxy" represented by $R_1$ and $R_4$ is optionally substituted, and substituents include halogen atoms; cyano; phenyl; trifluoromethyloxy; trifluoromethylthio; $C_{1-6}$ alkylcarbonyl optionally substituted by a halogen atom; or $C_{1-6}$ alkylcarbonyloxy optionally substituted by a halogen atom.

Phenyl in "benzyloxy" represented by $R_1$ and $R_4$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; formyl; azide; guanidyl; group —C(=NH)—NH$_2$; or group —CH=N—O—CH$_3$.

Phenyl in "benzoyloxy" represented by $R_2$, $R_3$ and $R_4$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; nitro; formyl; azide; guanidyl; group —C(=NH)—NH$_2$; or group —CH=N—O—CH$_3$. Preferred are halogen atoms, halogenated $C_{1-6}$ alkyl, cyano, and nitro.

Phenyl in "benzenesulfonyloxy" represented by $R_3$ and $R_4$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; formyl; azide; guanidyl; group —C(=NH)—NH$_2$; or group —CH=N—O—CH$_3$.

"$C_{1-6}$ alkylsulfonyloxy" represented by $R_2$, $R_3$ and $R_4$ is optionally substituted, and substituents include halogen atoms, cyano, phenyl, trifluoromethyloxy, or trifluoromethylthio.

"$C_{1-6}$ alkyloxycarbonyloxy" represented by $R_4$ is optionally substituted, and substituents include halogen atoms, cyano, phenyl, trifluoromethyloxy, or trifluoromethylthio.

"$C_{1-6}$ alkylaminocarbonyloxy" represented by $R_4$ is optionally substituted, and substituents include halogen atoms, cyano, phenyl, trifluoromethyloxy, or trifluoromethylthio.

"Phenyl" represented by $R_2'$ and $R_3'$ and phenyl in "benzyl" represented by $R_2'$ and $R_3'$ are optionally substituted, and substituents include halogen atoms, $C_{1-4}$ alkyl, $C_{1-4}$ alkyloxy, nitro, cyano, formyl, trifluoromethyloxy, acetyl, or acetyloxy.

Examples of "saturated or unsaturated five- or six-membered heterocyclic ring" in saturated or unsaturated five- or six-membered heterocyclic thiocarbonyloxy represented by $R_3$ and saturated or unsaturated five- or six-membered heterocyclic oxy, saturated or unsaturated five- or six-membered heterocyclic carbonyloxy, and saturated or unsaturated five- or six-membered heterocyclic thiocarbonyloxy represented by $R_4$ include thienyl, furyl, pyrrolyl, imidazolyl, pyrazolyl, isothiazoyl, isoxazolyl, thiazolyl, oxazolyl, pyridyl, pyrimidinyl, pyrazinyl, pyridazinyl, tetrahydropyranyl, piperidinyl, piperazinyl, morpholinyl, tetrahydropyranyl, pyrazinyl, thienyl, or mannosyl. Preferred are pyridyl, furanyl, thiazolyl, imidazolyl, tetrahydropyranyl, and mannosyl. More specific examples thereof include (2- or 3-)thienyl, (2- or 3-)furyl, (1-, 2- or 3-)pyrrolyl, (1-, 2-, 4- or 5-)imidazolyl, (1-, 3-, 4- or 5-)pyrazolyl, (3-, 4- or 5-)isothiazoyl, (3-, 4- or 5-)isoxazolyl, (2-, 4- or 5-)thiazolyl, (2-, 4- or 5-)oxazolyl, (2-, 3- or 4-)pyridyl or, (2-, 4-, 5- or 6-)pyrimidinyl, (2- or 3-)pyrazinyl, (3- or 4-)pyridazinyl, (2-, 3- or 4-)tetrahydropyranyl, (1-, 2-, 3- or 4-)piperidinyl, (1-, 2- or 3-)piperazinyl, and (2-, 3- or 4-)morpholinyl, preferably 3-pyridyl, 2-furanyl, 5-thiazolyl, 1-imidazolyl, 5-imidazolyl, or 2-tetrahydropyranyl, more preferably 2-tetrahydropyranyl, 2-pyrazinyl, or 3-pyridyl, particularly preferably 3-pyridyl.

The heterocyclic ring in the saturated or unsaturated five- or six-membered heterocyclic carbonyloxy and saturated or unsaturated five- or six-membered heterocyclic thiocarbonyloxy and thieno[3,2-b]pyridylcarbonyloxy and 1H-indolylcarbonyloxy represented by $R_4$ are optionally substituted, and substituents include halogen atoms, $C_{1-4}$ alkyl, $C_{1-4}$ alkyloxy, $C_{1-4}$ alkylthio, nitro, cyano, formyl, trifluoromethyloxy, trifluoromethyl, trifluoromethylthio, trifluoromethylsulfinyl, trifluoromethylsulfonyl, acetyl, acetyloxy, benzoyl, or $C_{1-4}$ alkyloxycarbonyl. Preferred are halogen atoms, $C_{1-4}$ alkyl, $C_{1-4}$ alkyloxy, and trifluoromethyl.

The heterocyclic ring in the saturated or unsaturated five- or six-membered heterocyclic oxy is optionally substituted, and substituents include hydroxyl, benzyloxy, a halogen atom, $C_{1-4}$ alkyl, $C_{1-4}$ alkyloxy, nitro, cyano, formyl, trifluoromethyloxy, trifluoromethyl, trifluoromethylthio, trifluoromethylsulfinyl, trifluoromethylsulfonyl, acetyl, or acetyloxy. Preferred are hydroxyl and benzyloxy.

Compounds of Formula (I)

In a preferred embodiment of the present invention, in compounds of formula (I), preferably, Het$_1$ represents 3-pyridyl.

Further, in a preferred embodiment of the present invention, in compounds of formula (I), $R_1$ represents hydroxyl, $C_{1-6}$ alkylcarbonyloxy, $C_{1-3}$ alkyloxy, or benzyloxy, or oxo in the absence of a hydrogen atom at the 13-position or the bond between 5-position and 13-position represents a double bond in the absence of $R_1$ and a hydrogen atom at the 5-position. More preferably, $R_1$ represents hydroxyl or $C_{1-6}$ alkylcarbonyloxy, or the bond between 5-position and 13-position represents a double bond in the absence of $R_1$ and a hydrogen atom at the 5-position. Still more preferably, $R_1$ represents hydroxyl.

In a preferred embodiment of the present invention, in the compounds of formula (I), $R_2$ represents hydroxyl, optionally substituted $C_{1-18}$ alkylcarbonyloxy, optionally substituted benzoyloxy, or $C_{1-3}$ alkylsulfonyloxy, more preferably optionally substituted $C_{1-18}$ alkylcarbonyloxy, still more preferably optionally substituted $C_{1-6}$ alkylcarbonyloxy, still more preferably optionally substituted cyclic $C_{3-6}$ alkylcarbonyloxy, particularly preferably cyclopropylcarbonyloxy.

In a preferred embodiment of the present invention, in the compounds of formula (I), $R_3$ represents a hydrogen atom, hydroxyl, optionally substituted $C_{1-18}$ alkylcarbonyloxy, optionally substituted benzoyloxy, $C_{1-6}$ alkylsulfonyloxy, optionally substituted benzenesulfonyloxy or saturated or unsaturated five- or six-membered heterocyclic thiocarbonyloxy, more preferably optionally substituted $C_{1-6}$ alkylcarbonyloxy or $C_{1-6}$ alkylsulfonyloxy, still more preferably optionally substituted $C_{1-6}$ alkylcarbonyloxy, still more preferably optionally substituted cyclic $C_{3-6}$ alkylcarbonyloxy, particularly preferably cyclopropylcarbonyloxy.

In a preferred embodiment of the present invention, in the compounds of formula (I), $R_2$ and $R_3$ together represent —O—CR$_2'$R$_3'$—O— wherein $R_2'$ and $R_3'$, which may be the same or different, represent a hydrogen atom, $C_{1-6}$ alkyl, $C_{1-3}$ alkyloxy, $C_{2-3}$ alkenyl, benzyl, or optionally substituted phenyl, or $R_2'$ and $R_3'$ together represent oxo or $C_{2-6}$ alkylene. More preferably, $R_2$ and $R_3$ together represent —O—CR$_2'$R$_3'$—O— wherein $R_2'$ and $R_3'$, which may be the same or different, represent a hydrogen atom, $C_{1-6}$ alkyl, or optionally substituted phenyl, or $R_2'$ and $R_3'$ together represent oxo or $C_{2-6}$ alkylene.

In a preferred embodiment of the present invention, in the compounds of formula (I), $R_4$ represents a hydrogen atom, hydroxyl, optionally substituted $C_{1-18}$ alkylcarbonyloxy, $C_{2-6}$ alkenylcarbonyloxy, $C_{2-6}$ alkynyl carbonyloxy, $C_{1-6}$ alkylsulfonyloxy, benzenesulfonyloxy, benzyloxy, $C_{1-3}$ alkyloxy, $C_{1-3}$ alkyloxy-$C_{1-3}$ alkyloxy, $C_{1-3}$ alkylthio-$C_{1-3}$ alkyloxy, $C_{1-3}$ alkyloxy-$C_{1-3}$ alkyloxy, optionally substituted $C_{1-3}$ alkyloxycarbonyloxy, optionally substituted $C_{1-6}$ alkylaminocarbonyloxy, optionally substituted benzoyloxy, saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. More preferably, $R_4$ represents a hydrogen atom, hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. Still more preferably, $R_4$ represents a hydrogen atom, hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy. Still more preferably, $R_4$ represents a hydrogen atom, hydroxyl, optionally substituted cyclic $C_{3-6}$ alkylcarbonyloxy, or optionally substituted benzoyloxy, or oxo in the absence of a hydrogen atom at the 7-position.

In another preferred embodiment of the present invention, in the compounds of formula (I), $Het_1$ represents 3-pyridyl, $R_1$ represents hydroxyl or $C_{1-6}$ alkylcarbonyloxy, or the bond between 5-position and 13-position represents a double bond in the absence of $R_1$ and a hydrogen atom at the 5-position, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, or $R_2$ and $R_3$ together represent —O—$CR_2'R_3'$—O— wherein $R_2'$ and $R_3'$, which may be the same or different, represent a hydrogen atom, $C_{1-6}$ alkyl, or optionally substituted phenyl, or $R_2'$ and $R_3'$ together represent oxo or $C_{2-6}$ alkylene, and $R_4$ represents a hydrogen atom, hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

In still another preferred embodiment of the present invention, in the compounds of formula (I), $Het_1$ represents 3-pyridyl, $R_1$ represents hydroxyl, $R_2$ represents optionally substituted $C_{1-6}$ alkylcarbonyloxy, and $R_3$ represents optionally substituted $C_{1-6}$ alkylcarbonyloxy or $C_{1-6}$ alkylsulfonyloxy, and $R_4$ represents a hydrogen atom, hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position, In a further preferred embodiment of the present invention, in the compounds of formula (I), $Het_1$ represents 3-pyridyl, $R_1$ represents hydroxyl, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, and $R_4$ represents a hydrogen atom, hydroxyl, optionally substituted $C_{1-6}$ alkylcarbonyloxy, optionally substituted benzoyloxy, saturated or unsaturated five- or six-membered heterocyclic oxy, optionally substituted saturated or unsaturated five- or six-membered heterocyclic carbonyloxy, or saturated or unsaturated five- or six-membered heterocyclic thiocarbonyloxy.

In another preferred embodiment of the present invention, in the compounds of formula (I), $Het_1$ represents 3-pyridyl, $R_1$ represents hydroxyl, and $R_2$ and $R_3$ represent optionally substituted cyclic $C_{3-6}$ alkylcarbonyloxy, $R_4$ represents a hydrogen atom, hydroxyl, optionally substituted cyclic $C_{3-6}$ alkylcarbonyloxy, optionally substituted benzoyloxy, or oxo in the absence of a hydrogen atom at the 7-position.

In still another preferred embodiment of the present invention, in the compounds of formula (I), $Het_1$ represents 3-pyridyl, $R_1$ represents hydroxyl, $R_2$ and $R_3$ represent cyclopropylcarbonyloxy, and $R_4$ preferably represents hydroxyl.

Agriculturally and horticulturally acceptable salts in the compounds of formula (I) include, for example, acid addition salts such as hydrochlorides, nitrates, sulfates, phosphates, or acetates.

Specific examples of pyripyropene derivatives of formula (I) or salts thereof preferable as the active ingredient of the composition according to the present invention include compounds shown in Tables 1 to 14 below. The pyripyropene derivatives shown in Tables 1 to 14 can be produced as described in Japanese Patent No. 2993767 (Japanese Patent Application Laid-Open No. 360895/1992) and WO 2006/129714. In the following tables, H(=) means that the bond between 5-position and 13-position represents a double bond in the absence of $R_1$ and a hydrogen atom at the 5-position.

TABLE 1

| Compound No. | $R_1$ | $R_2$ | $R_3$ | $R_4$ | $Het_1$ |
|---|---|---|---|---|---|
| 1 | OH | $OCOCH_3$ | $OCOCH_3$ | $OCOCH_2CH_3$ | 3-pyridyl |
| 2 | OH | $OCOCH_3$ | $OCOCH_3$ | $OCOCH_2CF_3$ | 3-pyridyl |
| 3 | OH | $OCOCH_3$ | $OCOCH_3$ | $OCOCH_2OCH_3$ | 3-pyridyl |
| 4 | OH | $OCOCH_3$ | $OCOCH_3$ | $OCOCH_2OCOCH_3$ | 3-pyridyl |
| 5 | OH | $OCOCH_3$ | $OCOCH_3$ | $OCOCH_2CH_2CN$ | 3-pyridyl |
| 6 | OH | $OCOCH_3$ | $OCOCH_3$ | $OCO(CH_2)_2CH_3$ | 3-pyridyl |
| 7 | OH | $OCOCH_3$ | $OCOCH_3$ | $OCO(CH_2)_3CH_3$ | 3-pyridyl |
| 8 | OH | $OCOCH_3$ | $OCOCH_3$ | $OCO(CH_2)_4CH_3$ | 3-pyridyl |
| 9 | OH | $OCOCH_3$ | $OCOCH_3$ | $OCO(CH_2)_5CH_3$ | 3-pyridyl |
| 10 | OH | $OCOCH_3$ | $OCOCH_3$ | $OCO(CH_2)_6CH_3$ | 3-pyridyl |
| 11 | OH | $OCOCH_3$ | $OCOCH_3$ | $OCO(CH_2)_{16}CH_3$ | 3-pyridyl |
| 12 | OH | $OCOCH_3$ | $OCOCH_3$ | $OCOCH(CH_3)_2$ | 3-pyridyl |
| 13 | OH | $OCOCH_3$ | $OCOCH_3$ | $OCOC(CH_3)_3$ | 3-pyridyl |
| 14 | OH | $OCOCH_3$ | $OCOCH_3$ | $OCOCH_2CH(CH_3)_2$ | 3-pyridyl |
| 15 | OH | $OCOCH_3$ | $OCOCH_3$ | $OCO(CH_2)_2CH(CH_3)_2$ | 3-pyridyl |
| 16 | OH | $OCOCH_3$ | $OCOCH_3$ | $OCO$-trans-$CH=CHCH_2CH_3$ | 3-pyridyl |
| 17 | OH | $OCOCH_3$ | $OCOCH_3$ | $OCOCH_2C\equiv CCH_3$ | 3-pyridyl |
| 18 | OH | $OCOCH_3$ | $OCOCH_3$ | $OCOC\equiv CCH_2CH_3$ | 3-pyridyl |

TABLE 1-continued

| Compound No. | R₁ | R₂ | R₃ | R₄ | Het₁ |
|---|---|---|---|---|---|
| 19 | OH | OCOCH₃ | OCOCH₃ | OCO(CH₂)₂C≡CH | 3-pyridyl |
| 20 | OH | OCOCH₃ | OCOCH₃ | OCO(CH₂)₂CH=CH₂ | 3-pyridyl |

TABLE 2

| Compound No. | R₁ | R₂ | R₃ | R₄ | Het₁ |
|---|---|---|---|---|---|
| 21 | OH | OCOCH₃ | OCOCH₃ | OCOCH₂C₆H₅ | 3-pyridyl |
| 22 | OH | OCOCH₃ | OCOCH₃ | OCO(CH₂)₂C₆H₅ | 3-pyridyl |
| 23 | OH | OCOCH₃ | OCOCH₃ | OCOC₆H₅ | 3-pyridyl |
| 24 | OH | OCOCH₃ | OCOCH₃ | OCO-(4-Br—C₆H₄) | 3-pyridyl |
| 25 | OH | OCOCH₃ | OCOCH₃ | OCO-(4-N₃—C₆H₄) | 3-pyridyl |
| 26 | OH | OCOCH₃ | OCOCH₃ | OCO-(4-OCF₃—C₆H₄) | 3-pyridyl |
| 27 | OH | OCOCH₃ | OCOCH₃ | OCO-(4-SO₂CF₃—C₆H₄) | 3-pyridyl |
| 28 | OH | OCOCH₃ | OCOCH₃ | OCO-(3-pyridyl) | 3-pyridyl |
| 29 | OH | OCOCH₃ | OCOCH₃ | OCO-(2-Cl-3-pyridyl) | 3-pyridyl |
| 30 | OH | OCOCH₃ | OCOCH₃ | OCO-(2-franyl) | 3-pyridyl |
| 31 | OH | OCOCH₃ | OCOCH₃ | OCO-(2-thiazolyl) | 3-pyridyl |
| 32 | OH | OCOCH₃ | OCOCH₃ | OCO-(2-Cl-5-thiazolyl) | 3-pyridyl |
| 33 | OH | OCOCH₃ | OCOCH₃ | OCO-(5-imidazolyl) | 3-pyridyl |
| 34 | OH | OCOCH₃ | OCOCH₃ | OCS-(1-imidazolyl) | 3-pyridyl |
| 35 | OH | OCOCH₃ | OCOCH₃ | OCOOCH₂C₆H₅ | 3-pyridyl |
| 36 | OH | OCOCH₃ | OCOCH₃ | OSO₂CH₃ | 3-pyridyl |
| 37 | OH | OCOCH₃ | OCOCH₃ | OSO₂C₆H₅ | 3-pyridyl |
| 38 | OH | OCOCH₃ | OCOCH₃ | OCONHCH₂CH₃ | 3-pyridyl |
| 39 | OH | OCOCH₃ | OCOCH₃ | OCONH(CH₂)₂CH₃ | 3-pyridyl |
| 40 | OH | OCOCH₃ | OCOCH₃ | OCONHCH₂C₆H₅ | 3-pyridyl |

TABLE 3

| Compound No. | R₁ | R₂ | R₃ | R₄ | Het₁ |
|---|---|---|---|---|---|
| 41 | OH | OCOCH₃ | OCOCH₃ | OCH₂C₆H₅ | 3-pyridyl |
| 42 | OH | OCOCH₃ | OCOCH₃ | OCH₂SCH₃ | 3-pyridyl |
| 43 | OH | OCOCH₃ | OCOCH₃ | OCH₂OCH₃ | 3-pyridyl |
| 44 | OH | OCOCH₃ | OCOCH₃ | OCH₂OCH₂CH₂OCH₃ | 3-pyridyl |
| 45 | OH | OCOCH₃ | OCOCH₃ | O-(2-tetrahydropyranyl) | 3-pyridyl |
| 46 | OH | OCOCH₃ | OCOCH₃ | O-(tetra-O-benzyl-mannosyl) | 3-pyridyl |
| 47 | OH | OCOCH₃ | OCOCH₃ | H | 3-pyridyl |
| 48 | OH | OCOCH₃ | OCOCH₃ | OCO—c-C₃H₅ | 3-pyridyl |
| 49 | OH | OCOCH₃ | OCOCH₃ | OH | 3-pyridyl |
| 50 | OH | OCOCH₃ | OCOCH₃ | =O | 3-pyridyl |
| 51 | OH | OCOCH₃ | OCOCH₂CH₃ | OCOCH₃ | 3-pyridyl |
| 52 | OH | OCOCH₃ | OCOCH₂CH₃ | OCOCH₂CH₃ | 3-pyridyl |
| 53 | OH | OCOCH₃ | OCOCH₂CH₃ | H | 3-pyridyl |
| 54 | OH | OCOCH₃ | OCO(CH₂)₂CH₃ | OCOCH₃ | 3-pyridyl |
| 55 | OH | OCOCH₃ | OCO(CH₂)₂CH₃ | OH | 3-pyridyl |
| 56 | OH | OCOCH₃ | OCO(CH₂)₃CH₃ | OCOCH₃ | 3-pyridyl |
| 57 | OH | OCOCH₃ | OCOCH(CH₃)₂ | OCOCH₃ | 3-pyridyl |
| 58 | OH | OCOCH₃ | OCOC₆H₅ | OCOCH₃ | 3-pyridyl |
| 59 | OH | OCOCH₃ | OCOC₆H₅ | OH | 3-pyridyl |
| 60 | OH | OCOCH₃ | OCS-(1-imidazoyl) | OCOCH₃ | 3-pyridyl |

TABLE 4

| Compound No. | R₁ | R₂ | R₃ | R₄ | Het₁ |
|---|---|---|---|---|---|
| 61 | OH | OCOCH₃ | OSO₂CH₃ | OCOCH₃ | 3-pyridyl |
| 62 | OH | OCOCH₃ | OSO₂CH₃ | OCO(CH₂)₃CH₃ | 3-pyridyl |
| 63 | OH | OCOCH₃ | OSO₂C₆H₅ | OCOCH₃ | 3-pyridyl |
| 64 | OH | OCOCH₃ | OSO₂CH₂CH₃ | OCOCH₃ | 3-pyridyl |
| 65 | OH | OCOCH₃ | OSO₂CH₂CH₂CH₃ | OCOCH₃ | 3-pyridyl |
| 66 | OH | OCOCH₃ | OSO₂CH₂CH₃ | OH | 3-pyridyl |
| 67 | OH | OCOCH₃ | OSO₂CH₂CH₂CH₃ | OH | 3-pyridyl |
| 68 | OH | OCOCH₃ | OH | OH | 3-pyridyl |
| 69 | OH | OCOCH₃ | OH | OCOCH₃ | 3-pyridyl |
| 70 | OH | OCOCH₃ | H | H | 3-pyridyl |
| 71 | OH | OCOCH₃ | H | OCOCH₂CH₃ | 3-pyridyl |

TABLE 4-continued

| Compound No. | $R_1$ | $R_2$ | $R_3$ | $R_4$ | $Het_1$ |
|---|---|---|---|---|---|
| 72 | OH | $OCOCH_2CH_3$ | $OCOCH_3$ | $OCOCH_3$ | 3-pyridyl |
| 73 | OH | $OCOCH_2CH_3$ | $OCOCH_2CH_3$ | OH | 3-pyridyl |
| 74 | OH | $OCOCH_2CH_3$ | $OCOCH_2CH_3$ | $OCOCH_3$ | 3-pyridyl |
| 75 | OH | $OCOCH_2CH_3$ | $OCOCH_3$ | $OCOCH_2CH_3$ | 3-pyridyl |
| 76 | OH | $OCOCH_2CH_3$ | $OCOCH_2CH_3$ | $OCOCH_2CH_3$ | 3-pyridyl |
| 77 | OH | $OCOCH_2CH_3$ | $OCOCH_2CH_3$ | $OCOC_6H_5$ | 3-pyridyl |
| 78 | OH | $OCOCH_2CH_3$ | $OCOCH_2CH_3$ | H | 3-pyridyl |
| 79 | OH | $OCOCH_2CH_3$ | H | H | 3-pyridyl |
| 80 | OH | $OCO(CH_2)_2CH_3$ | $OCOCH_3$ | $OCOCH_3$ | 3-pyridyl |

TABLE 5

| Compound No. | $R_1$ | $R_2$ | $R_3$ | $R_4$ | $Het_1$ |
|---|---|---|---|---|---|
| 81 | OH | $OCO(CH_2)_2CH_3$ | $OCO(CH_2)_2CH_3$ | OH | 3-pyridyl |
| 82 | OH | $OCO(CH_2)_2CH_3$ | $OCO(CH_2)_2CH_3$ | $OCO(CH_2)_2CH_3$ | 3-pyridyl |
| 83 | OH | $OCO(CH_2)_2CH_3$ | $OCO(CH_2)_2CH_3$ | $OCOCH_3$ | 3-pyridyl |
| 84 | OH | $OCO(CH_2)_3CH_3$ | $OCOCH_3$ | $OCOCH_3$ | 3-pyridyl |
| 85 | OH | $OCO(CH_2)_3CH_3$ | $OCO(CH_2)_3CH_3$ | $OCO(CH_2)_3CH_3$ | 3-pyridyl |
| 86 | OH | $OCO(CH_2)_3CH_3$ | $OSO_2CH_3$ | $OCO(CH_2)_3CH_3$ | 3-pyridyl |
| 87 | OH | $OCO(CH_2)_3CH_3$ | $OSO_2CH_3$ | OH | 3-pyridyl |
| 88 | OH | $OCO(CH_2)_{16}CH_3$ | $OCO(CH_2)_{16}CH_3$ | $OCO(CH_2)_{16}CH_3$ | 3-pyridyl |
| 89 | OH | $OCOCH(CH_3)_2$ | $OCOCH_3$ | $OCOCH_3$ | 3-pyridyl |
| 90 | OH | $OCOCH(CH_3)_2$ | $OCOCH(CH_3)_2$ | $OCOCH(CH_3)_2$ | 3-pyridyl |
| 91 | OH | $OCOC(CH_3)_3$ | $OCOC(CH_3)_3$ | $OCOC(CH_3)_3$ | 3-pyridyl |
| 92 | OH | $OCOC_6H_5$ | $OCOCH_3$ | $OCOCH_3$ | 3-pyridyl |
| 93 | OH | $OCOC_6H_5$ | $OSO_2CH_3$ | OH | 3-pyridyl |
| 94 | OH | $OCOC_6H_5$ | $OSO_2CH_3$ | $OCOCH_3$ | 3-pyridyl |
| 95 | OH | $OCOC_6H_5$ | $OSO_2CH_3$ | $OCO(CH_2)_3CH_3$ | 3-pyridyl |
| 96 | OH | $OCO-(4-Br-C_6H_4)$ | $OCO-(4-Br-C_6H_4)$ | $OCO-(4-Br-C_6H_4)$ | 3-pyridyl |
| 97 | OH | $OCO-(4-N_3-C_6H_4)$ | $OSO_2CH_3$ | $OCOCH_3$ | 3-pyridyl |
| 98 | OH | $OSO_2CH_3$ | $OSO_2CH_3$ | OH | 3-pyridyl |
| 99 | OH | $OSO_2CH_3$ | $OSO_2CH_3$ | $OSO_2CH_3$ | 3-pyridyl |
| 100 | OH | $OSO_2CH_3$ | $OSO_2CH_3$ | $OCOCH_3$ | 3-pyridyl |

TABLE 6

| Compound No. | $R_1$ | $R_2$ | $R_3$ | $R_4$ | $Het_1$ |
|---|---|---|---|---|---|
| 101 | OH | $OSO_2CH_3$ | OH | OH | 3-pyridyl |
| 102 | OH | OH | OH | OH | 3-pyridyl |
| 103 | OH | OH | OH | $OCOCH_3$ | 3-pyridyl |
| 104 | OH | OH | OH | $OCO(CH_2)_3CH_3$ | 3-pyridyl |
| 105 | OH | OH | OH | $OCH_2OCH_2CH_2OCH_3$ | 3-pyridyl |
| 106 | OH | OH | $OCOCH_3$ | OH | 3-pyridyl |
| 107 | OH | OH | $OCOCH_2CH_3$ | OH | 3-pyridyl |
| 108 | OH | OH | $OCO(CH_2)_2CH_3$ | OH | 3-pyridyl |
| 109 | OH | OH | $OCO(CH_2)_3CH_3$ | OH | 3-pyridyl |
| 110 | OH | OH | $OCOCH(CH_3)_2$ | OH | 3-pyridyl |
| 111 | OH | OH | $OSO_2CH_3$ | OH | 3-pyridyl |
| 112 | OH | OH | $OSO_2CH_2CH_3$ | OH | 3-pyridyl |
| 113 | OH | OH | $OSO_2CH_2CH_2CH_3$ | OH | 3-pyridyl |
| 114 | OH | OH | $OSO_2CH(CH_3)_2$ | OH | 3-pyridyl |
| 115 | OH | OH | $OSO_2C_6H_5$ | OH | 3-pyridyl |
| 116 | OH | OH | $OSO_2-(4-CH_3-C_6H_4)$ | OH | 3-pyridyl |
| 117 | OH | OH | $OCO-(4-Br-C_6H_4)$ | OH | 3-pyridyl |
| 118 | OH | OH | $OCO(CH_2)_3CH_3$ | $OCO(CH_2)_3CH_3$ | 3-pyridyl |
| 119 | OH | OH | $OSO_2CH_3$ | $OSO_2CH_3$ | 3-pyridyl |
| 120 | OH | OH | $OSO_2CH_3$ | $OCOCH_3$ | 3-pyridyl |

TABLE 7

| Compound No. | $R_1$ | $R_2$ | $R_3$ | $R_4$ | $Het_1$ |
|---|---|---|---|---|---|
| 121 | OH | OH | $OSO_2CH_3$ | $OCOCH_3$ | 3-pyridyl |
| 122 | OH | OH | $OSO_2CH_3$ | $OCO(CH_2)_3CH_3$ | 3-pyridyl |
| 123 | OH | OH | $OSO_2C_6H_5$ | $OCOCH_3$ | 3-pyridyl |
| 124 | OH | OH | $OSO_2C_6H_5$ | $OSO_2C_6H_5$ | 3-pyridyl |
| 125 | OH | —O—$CH(CH_3)$—O— | | $OCO(CH_2)_3CH_3$ | 3-pyridyl |
| 126 | OH | —O—$CH(C_2H_5)$—O— | | OH | 3-pyridyl |

TABLE 7-continued

| Compound No. | R$_1$ | R$_2$ | R$_3$ | R$_4$ | Het$_1$ |
|---|---|---|---|---|---|
| 127 | OH | —O—CH(C$_2$H$_5$)—O— | | OCO(CH$_2$)$_3$CH$_3$ | 3-pyridyl |
| 128 | OH | —O—CH(CH=CH$_2$)—O— | | OH | 3-pyridyl |
| 129 | OH | —O—CH(CH=CH$_2$)—O— | | OCO(CH$_2$)$_3$CH$_3$ | 3-pyridyl |
| 130 | OH | —O—CH(CH(CH$_3$)$_2$)—O— | | OH | 3-pyridyl |
| 131 | OH | —O—CH(CH(CH$_3$)$_2$)—O— | | OCO(CH$_2$)$_3$CH$_3$ | 3-pyridyl |
| 132 | OH | —O—CH(OCH$_3$)—O— | | OH | 3-pyridyl |
| 142 | OH | —O—CH(OCH$_3$)—O— | | OCO(CH$_2$)$_3$CH$_3$ | 3-pyridyl |
| 133 | OH | —O—CH(C(CH$_3$)$_3$)—O— | | OCO(CH$_2$)$_3$CH$_3$ | 3-pyridyl |
| 134 | OH | —O—CH(CH$_2$C$_6$H$_5$)—O— | | OH | 3-pyridyl |
| 135 | OH | —O—C(CH$_3$)$_2$—O— | | OH | 3-pyridyl |
| 136 | OH | —O—C(CH$_3$)$_2$—O— | | OCOCH$_3$ | 3-pyridyl |
| 137 | OH | —O—C(CH$_3$)$_2$—O— | | OCO(CH$_2$)$_3$CH$_3$ | 3-pyridyl |
| 138 | OH | —O—C(CH$_3$)(C$_6$H$_5$)—O— | | OH | 3-pyridyl |
| 139 | OH | —O—C(CH$_3$)(C$_6$H$_5$)—O— | | OCO(CH$_2$)$_3$CH$_3$ | 3-pyridyl |
| 140 | OH | —O—CH(C$_6$H$_5$)—O— | | OH | 3-pyridyl |

TABLE 8

| Compound No. | R$_1$ | R$_2$ | R$_3$ | R$_4$ | Het$_1$ |
|---|---|---|---|---|---|
| 141 | OH | —O—CH(C$_6$H$_5$)—O— | | OCOCH$_3$ | 3-pyridyl |
| 143 | OH | —O—CH(C$_6$H$_5$)—O— | | OCO(CH$_2$)$_3$CH$_3$ | 3-pyridyl |
| 144 | OH | —O—CH(3-CH$_3$—C$_6$H$_4$)—O— | | OH | 3-pyridyl |
| 145 | OH | —O—CH(3-CH$_3$—C$_6$H$_4$)—O— | | OCO(CH$_2$)$_3$CH$_3$ | 3-pyridyl |
| 146 | OH | —O—CH(2-CH$_3$—C$_6$H$_4$)—O— | | OH | 3-pyridyl |
| 147 | OH | —O—CH(4-CH$_3$—C$_6$H$_4$)—O— | | OCO(CH$_2$)$_3$CH$_3$ | 3-pyridyl |
| 148 | OH | —O—CH(3-F—C$_6$H$_4$)—O— | | OH | 3-pyridyl |
| 149 | OH | —O—CH(2-F—C$_6$H$_4$)—O— | | OCO(CH$_2$)$_3$CH$_3$ | 3-pyridyl |
| 150 | OH | —O—CH(4-F—C$_6$H$_4$)—O— | | OCO(CH$_2$)$_3$CH$_3$ | 3-pyridyl |
| 151 | OH | —O—CH(4-NO$_2$—C$_6$H$_4$)—O— | | OH | 3-pyridyl |
| 152 | OH | —O—CH(4-NO$_2$—C$_6$H$_4$)—O— | | OCO(CH$_2$)$_3$CH$_3$ | 3-pyridyl |
| 153 | OH | —O—CH(4-OCH$_3$—C$_6$H$_4$)—O— | | OH | 3-pyridyl |
| 154 | OH | —O—CH(4-OCH$_3$—C$_6$H$_4$)—O— | | OCO(CH$_2$)$_3$CH$_3$ | 3-pyridyl |
| 155 | OH | —O—C(spiro-c-C$_5$H$_8$)—O— | | OH | 3-pyridyl |
| 156 | OH | —O—C(spiro-c-C$_5$H$_8$)—O— | | OCO(CH$_2$)$_3$CH$_3$ | 3-pyridyl |
| 157 | OH | —O—C(spiro-c-C$_6$H$_{10}$)—O— | | OH | 3-pyridyl |
| 158 | OH | —O—C(spiro-c-C$_6$H$_{10}$)—O— | | OCO(CH$_2$)$_3$CH$_3$ | 3-pyridyl |
| 159 | OH | —O—CO—O— | | OH | 3-pyridyl |
| 160 | OH | —O—CO—O— | | OCO-1-imidazolyl | 3-pyridyl |

TABLE 9

| Compound No. | R$_1$ | R$_2$ | R$_3$ | R$_4$ | Het$_1$ |
|---|---|---|---|---|---|
| 161 | OH | —O—CO—O— | | OCO(CH$_2$)$_3$CH$_3$ | 3-pyridyl |
| 162 | OCOCH$_3$ | OCOCH$_3$ | OCOCH$_3$ | OCOCH$_3$ | 3-pyridyl |
| 163 | OCOCH$_3$ | OCOCH$_3$ | OCOCH$_3$ | OH | 3-pyridyl |
| 164 | OCOCH$_3$ | OCOCH$_3$ | OCO(CH$_2$)$_2$CH$_3$ | OCOCH$_3$ | 3-pyridyl |
| 165 | OCOCH$_3$ | OH | OH | OCOCH$_3$ | 3-pyridyl |
| 166 | OCOCH$_3$ | OCOCH$_2$CH$_3$ | OCOCH$_2$CH$_3$ | OCOCH$_2$CH$_3$ | 3-pyridyl |
| 167 | OCOCH$_2$CH$_3$ | OCOCH$_2$CH$_3$ | OCOCH$_2$CH$_3$ | OCOCH$_2$CH$_3$ | 3-pyridyl |
| 168 | OCOCH$_2$CH$_3$ | OCOCH$_3$ | OCOCH$_3$ | OCOCH$_3$ | 3-pyridyl |
| 169 | OCO(CH$_2$)$_3$CH$_3$ | OCOCH$_3$ | OCOCH$_3$ | OCOCH$_3$ | 3-pyridyl |
| 170 | OCO(CH$_2$)$_3$CH$_3$ | OCOCH$_3$ | OCOCH$_3$ | OCO(CH$_2$)$_3$CH$_3$ | 3-pyridyl |
| 171 | OCO(CH$_2$)$_2$CH$_3$ | OCOCH$_3$ | OCOCH$_3$ | OCOCH$_3$ | 3-pyridyl |
| 172 | OCH$_3$ | OCOCH$_3$ | OCOCH$_3$ | OCOCH$_3$ | 3-pyridyl |
| 173 | H(=) | OCOCH$_3$ | OSO$_2$CH$_3$ | OH | 3-pyridyl |
| 174 | H(=) | OCOC$_6$H$_5$ | OSO$_2$CH$_3$ | OCOCH$_3$ | 3-pyridyl |
| 175 | H(=) | OH | OH | OCOCH$_3$ | 3-pyridyl |
| 176 | H(=) | OCOCH$_3$ | OCOCH$_3$ | =O | 3-pyridyl |
| 177 | H(=) | —O—CH(C$_6$H$_5$)—O— | | OCOCH$_3$ | 3-pyridyl |
| 178 | H(=) | —O—CH(CH(CH$_3$)$_2$)—O— | | OH | 3-pyridyl |
| 179 | H(=) | —O—CH(4-NO$_2$—C$_6$H$_4$)—O— | | OH | 3-pyridyl |
| 180 | H(=) | OCOCH$_3$ | OCOCH$_3$ | OCOCH$_3$ | 3-pyridyl |

TABLE 10

| Compound No. | $R_1$ | $R_2$ | $R_3$ | $R_4$ | $Het_1$ |
|---|---|---|---|---|---|
| 181 | H(=) | OH | OH | OH | 3-pyridyl |
| 182 | H(=) | OCOCH$_3$ | OCOCH$_3$ | OH | 3-pyridyl |
| 183 | H(=) | OCOCH$_3$ | OCOCH$_3$ | OCH$_2$SCH$_3$ | 3-pyridyl |
| 184 | H(=) | OCOCH$_3$ | OCOCH$_3$ | OCH$_2$OCH$_3$ | 3-pyridyl |
| 185 | H(=) | OCOCH$_3$ | OCOCH$_3$ | OCO(CH$_2$)$_3$CH$_3$ | 3-pyridyl |
| 186 | H(=) | OCOCH$_3$ | OCOCH$_3$ | OCO(CH$_2$)$_2$Ph | 3-pyridyl |
| 187 | H(=) | OCOCH$_3$ | OSO$_2$CH$_3$ | OCOCH$_3$ | 3-pyridyl |
| 188 | H(=) | OCOCH$_2$CH$_3$ | OCOCH$_2$CH$_3$ | OCOCH$_2$CH$_3$ | 3-pyridyl |
| 189 | H(=) | OCOCH$_2$CH$_3$ | OCOCH$_2$CH$_3$ | OH | 3-pyridyl |
| 190 | H(=) | OH | OSO$_2$CH$_3$ | OH | 3-pyridyl |
| 191 | H(=) | OH | OH | OCO(CH$_2$)$_3$CH$_3$ | 3-pyridyl |
| 192 | H(=) | —O—C(CH$_3$)$_2$—O— | | OH | 3-pyridyl |
| 193 | H(=) | —O—C(CH$_3$)$_2$—O— | | OCO(CH$_2$)$_3$CH$_3$ | 3-pyridyl |
| 194 | H(=) | —O—CH(C$_6$H$_5$)—O— | | OH | 3-pyridyl |
| 195 | H(=) | —O—CH(C$_6$H$_5$)—O— | | OCO(CH$_2$)$_3$CH$_3$ | 3-pyridyl |
| 196 | H(=) | —O—CH(4-OCH$_3$—C$_6$H$_4$)—O— | | OH | 3-pyridyl |
| 197 | H(=) | —O—CH(C$_2$H$_5$)—O— | | OH | 3-pyridyl |
| 198 | H(=) | —O—CH(C(CH$_3$)$_2$)—O— | | OH | 3-pyridyl |
| 199 | H(=) | —O—CH(CH$_2$C$_6$H$_5$)—O— | | OH | 3-pyridyl |
| 200 | =O | OH | OH | OH | 3-pyridyl |

TABLE 11

| Compound No. | $R_1$ | $R_2$ | $R_3$ | $R_4$ | $Het_1$ |
|---|---|---|---|---|---|
| 201 | =O | OCOCH$_3$ | OCOCH$_3$ | =O | 3-pyridyl |
| 202 | =O | OCOCH$_3$ | OCOCH$_3$ | OH | 3-pyridyl |
| 203 | =O | OCOCH$_3$ | OCOCH$_3$ | OCOCH$_3$ | 3-pyridyl |
| 204 | =O | OCOCH$_2$CH$_3$ | OCOCH$_2$CH$_3$ | OCOCH$_2$CH$_3$ | 3-pyridyl |
| 205 | OH | OCOCH$_2$CH$_3$ | OCOCH$_2$CH$_3$ | OCO-(3-pyridyl) | 3-pyridyl |
| 206 | OH | OCOCH$_2$CH$_3$ | OCOCH$_2$CH$_3$ | OCOCH(CH$_3$)$_2$ | 3-pyridyl |
| 207 | OH | OCOCH$_2$CH$_3$ | OCOCH$_2$CH$_3$ | OCOC(CH$_3$)$_3$ | 3-pyridyl |
| 208 | OH | OCOCH$_2$CH$_3$ | OCOCH$_2$CH$_3$ | OCO-(4-CF$_3$—C$_6$H$_4$) | 3-pyridyl |
| 209 | OH | OCOCH$_2$CH$_3$ | OCOCH$_2$CH$_3$ | OCO-(1-imidazolyl) | 3-pyridyl |
| 210 | OH | OCOCH$_2$CH$_3$ | OCOCH$_2$CH$_3$ | OCONH(CH$_2$)$_2$CH$_3$ | 3-pyridyl |
| 211 | OH | OCOCH$_2$CH$_3$ | OCOCH$_2$CH$_3$ | O-(2-tetrahydropyranyl) | 3-pyridyl |
| 212 | OH | OCOCH$_2$CH$_3$ | OCOCH$_2$CH$_3$ | OCO-(6-Cl-3-pyridyl) | 3-pyridyl |
| 213 | OH | OCOCH$_2$CH$_3$ | OCOCH$_2$CH$_3$ | OCO—c-C$_3$H$_5$ | 3-pyridyl |
| 214 | OH | OCOCH$_2$CH$_3$ | OCOCH$_2$CH$_3$ | OCO—c-C$_4$H$_7$ | 3-pyridyl |
| 215 | OH | OCOCH$_2$CH$_3$ | OCOCH$_2$CH$_3$ | OCOCH=CH | 3-pyridyl |
| 216 | OH | OCOCH$_2$CH$_3$ | OCOCH$_2$CH$_3$ | OCO-(4-pyridyl) | 3-pyridyl |
| 217 | OH | OCOCH$_2$CH$_3$ | OCOCH$_2$CH$_3$ | OCO-(2-pyridyl) | 3-pyridyl |
| 218 | OH | OCO—c-C$_3$H$_5$ | OCO—c-C$_3$H$_5$ | OCO—c-C$_3$H$_5$ | 3-pyridyl |
| 219 | OH | OCO—c-C$_4$H$_7$ | OCO—c-C$_4$H$_7$ | OCO—c-C$_4$H$_7$ | 3-pyridyl |
| 220 | OH | OCOC$_6$H$_5$ | OCOC$_6$H$_5$ | OCOC$_6$H$_5$ | 3-pyridyl |

TABLE 12

| Compound No. | $R_1$ | $R_2$ | $R_3$ | $R_4$ | $Het_1$ |
|---|---|---|---|---|---|
| 221 | OH | OCOCH$_2$CH$_3$ | OCOCH$_2$CH$_3$ | OCO-(6-CF$_3$-3-pyridyl) | 3-pyridyl |
| 222 | OH | OCOCH$_2$CH$_3$ | OCOCH$_2$CH$_3$ | OCO-(4-CF$_3$-3-pyridyl) | 3-pyridyl |
| 223 | OH | OCOCH$_2$CH$_3$ | OCOCH$_2$CH$_3$ | OCOCH$_2$CF$_3$ | 3-pyridyl |
| 224 | OH | OCOCH$_2$CH$_3$ | OCOCH$_2$CH$_3$ | OCOCH$_2$CF$_3$ | 3-pyridyl |
| 225 | =O | OCOCH$_2$CH$_3$ | OCOCH$_2$CH$_3$ | OCOCH$_2$CH$_3$ | 6-Cl-3-pyridyl |
| 226 | OH | OCOCH$_2$CH$_3$ | OCOCH$_2$CH$_3$ | OCOCH$_2$CH$_3$ | 6-Cl-3-pyridyl |
| 227 | OH | OCOCH$_2$CH$_3$ | OCOCH$_2$CH$_3$ | OCO-(3-F-4-pyridyl) | 3-pyridyl |
| 228 | OH | OCOCH$_2$CH$_3$ | OCOCH$_2$CH$_3$ | OCO-(3-Cl-4-pyridyl) | 3-pyridyl |
| 229 | OH | OCOCH$_2$CH$_3$ | OCOCH$_2$CH$_3$ | OCO-(3-CH$_3$-2-pyridyl) | 3-pyridyl |
| 230 | OH | OCOCH$_2$CH$_3$ | OCOCH$_2$CH$_3$ | OCO-(3-COC$_6$H$_5$-2-pyridyl) | 3-pyridyl |
| 231 | OH | OCOCH$_2$CH$_3$ | OCOCH$_2$CH$_3$ | OCO-(3-OCH$_2$CH$_2$CH$_3$-2-pyridyl) | 3-pyridyl |
| 232 | OH | OCOCH$_2$CH$_3$ | OCOCH$_2$CH$_3$ | OCO-(6-F-3-pyridyl) | 3-pyridyl |
| 233 | OH | OCO—c-C$_5$H$_9$ | OCO—c-C$_5$H$_9$ | OCO—c-C$_5$H$_9$ | 3-pyridyl |
| 234 | OH | OCO—c-C$_6$H$_{11}$ | OCO—c-C$_6$H$_{11}$ | OCO—c-C$_6$H$_{11}$ | 3-pyridyl |
| 235 | OH | OCOCH$_2$CN | OCOCH$_2$CN | OCOCH$_2$CN | 3-pyridyl |
| 236 | OCOCH$_2$—c-C$_3$H$_5$ | OCOCH$_2$—c-C$_3$H$_5$ | OCOCH$_2$—c-C$_3$H$_5$ | OCOCH$_2$—c-C$_3$H$_5$ | 3-pyridyl |
| 237 | OH | OCOCH$_2$—c-C$_3$H$_5$ | OCOCH$_2$—c-C$_3$H$_5$ | OCOCH$_2$—c-C$_3$H$_5$ | 3-pyridyl |
| 238 | OH | OCO-(1-CH$_3$-2,2-F$_2$—c-C$_3$H$_2$) | OCO-(1-CH$_3$-2,2-F$_2$—c-C$_3$H$_2$) | OCO-(1-CH$_3$-2,2-F$_2$—c-C$_3$H$_2$) | 3-pyridyl |

TABLE 12-continued

| Compound No. | $R_1$ | $R_2$ | $R_3$ | $R_4$ | $Het_1$ |
|---|---|---|---|---|---|
| 239 | OH | OCOCH$_2$CH$_3$ | OCOCH$_2$CH$_3$ | OCO-(4-CH$_3$-3-pyridyl) | 3-pyridyl |
| 240 | OH | OCOCH$_2$CH$_3$ | OCOCH$_2$CH$_3$ | OCO-(4-Cl-3-pyridyl) | 3-pyridyl |

TABLE 13

| Compound No. | $R_1$ | $R_2$ | $R_3$ | $R_4$ | $Het_1$ |
|---|---|---|---|---|---|
| 241 | OH | OCOCH$_2$CH$_3$ | OCOCH$_2$CH$_3$ | OCO-(4-COOCH$_3$-3-pyridyl) | 3-pyridyl |
| 242 | OH | OCOCH$_2$CH$_3$ | OCOCH$_2$CH$_3$ | OCO-[5-(CF$_3$)-thieno[3,2-b]-pyridin-6-yl] | 3-pyridyl |
| 243 | OH | OCOCH$_2$CH$_3$ | OCOCH$_2$CH$_3$ | OCO-(2-CN—C$_6$H$_4$) | 3-pyridyl |
| 244 | OH | OCOCH$_2$CH$_3$ | OCOCH$_2$CH$_3$ | OCO-(2-CF$_3$—C$_6$H$_4$) | 3-pyridyl |
| 245 | OH | OCOCH$_2$CH$_3$ | OCOCH$_2$CH$_3$ | OCO-(2-F—C$_6$H$_4$) | 3-pyridyl |
| 246 | OH | OCOCH$_2$CH$_3$ | OCOCH$_2$CH$_3$ | OCO-(2-NO$_2$—C$_6$H$_4$) | 3-pyridyl |
| 247 | OH | OCOCH$_2$CH$_3$ | OCOCH$_2$CH$_3$ | OCO-(2-Cl-3-pyridyl) | 3-pyridyl |
| 248 | OH | OCOCH$_2$CH$_3$ | OCOCH$_2$CH$_3$ | OCO(2-Cl-6-CH$_3$-3-pyridyl) | 3-pyridyl |
| 249 | OH | OCOCH$_2$CH$_3$ | OCOCH$_2$CH$_3$ | OCH$_2$OCH$_3$ | 3-pyridyl |
| 250 | OH | OCO-(2,2-F$_2$—c-C$_3$H$_3$) | OCO-(2,2-F$_2$—c-C$_3$H$_3$) | OCO-(2,2-F$_2$—c-C$_3$H$_3$) | 3-pyridyl |
| 251 | OH | OCOCH$_2$CH$_3$ | OCOCH$_2$CH$_3$ | OCO-(3-SC(CH$_3$)$_3$-2-pyridyl) | 3-pyridyl |
| 252 | OH | OCOCH$_2$CH$_3$ | OCOCH$_2$CH$_3$ | OCO-(3,5-2F-2-pyridyl) | 3-pyridyl |
| 253 | OH | OCOCH$_2$CH$_3$ | OCOCH$_2$CH$_3$ | OCO-2-pyrazinyl | 3-pyridyl |
| 254 | OH | OCOCH$_2$CH$_3$ | OCOCH$_2$CH$_3$ | OCO-4-thiazolyl | 3-pyridyl |
| 255 | OH | OCOCH$_2$CH$_3$ | OCOCH$_2$CH$_3$ | OCO-(3-Cl-2-thienyl) | 3-pyridyl |
| 256 | OH | OCOCH$_2$CH$_3$ | OCOCH$_2$CH$_3$ | OCO-(6-CH$_3$-3-pyridyl) | 3-pyridyl |
| 257 | OH | OCOCH$_2$CH$_3$ | OCOCH$_2$CH$_3$ | OCO-(6-Cl-2-pyridyl) | 3-pyridyl |
| 258 | OH | OCOCH$_2$CH$_3$ | OCOCH$_2$CH$_3$ | OCO-(6-F-2-pyridyl) | 3-pyridyl |
| 259 | OH | OCOCH$_2$CH$_3$ | OCOCH$_2$CH$_3$ | OCO-(1-CH$_3$-1H-indolyl) | 3-pyridyl |
| 260 | OH | OCOCH$_2$CH$_3$ | OCOCH$_2$CH$_3$ | OCO-(3-Cl-2-pyridyl) | 3-pyridyl |

TABLE 14

| Compound No. | $R_1$ | $R_2$ | $R_3$ | $R_4$ | $Het_1$ |
|---|---|---|---|---|---|
| 261 | OH | OCO—c-C$_3$H$_5$ | OCO—c-C$_3$H$_5$ | OH | 3-pyridyl |
| 262 | OH | OCOCH$_2$CH$_3$ | OCOCH$_2$CH$_3$ | OCO—(2-F-3-pyridyl) | 3-pyridyl |
| 263 | OH | OCOCH$_2$CH$_3$ | OCOCH$_2$CH$_3$ | OCO—(4-CN—C$_6$H$_4$) | 3-pyridyl |
| 264 | OH | OCOCH$_2$CH$_3$ | OCOCH$_2$CH$_3$ | OCO—(3-CN—C$_6$H$_4$) | 3-pyridyl |
| 265 | OH | OCOCH$_2$CH$_3$ | OCOCH$_2$CH$_3$ | OCO—(3-CF$_3$—C$_6$H$_4$) | 3-pyridyl |
| 266 | OH | OCOCH$_2$CH$_3$ | OCOCH$_2$CH$_3$ | OCOCH$_2$(2-pyridyl) | 3-pyridyl |
| 267 | OH | OCOCH$_2$CH$_3$ | OCOCH$_2$CH$_3$ | OCOCH$_2$(3-pyridyl) | 3-pyridyl |
| 268 | OH | OCOCH$_2$CH$_3$ | OCOCH$_2$CH$_3$ | OCOCH$_2$S(4-pyridyl) | 3-pyridyl |
| 269 | OH | OCO—c-C$_3$H$_5$ | OCO—c-C$_3$H$_5$ | OCO—(2-CN—C$_6$H$_4$) | 3-pyridyl |
| 270 | OH | OCO—c-C$_3$H$_5$ | OCO—c-C$_3$H$_5$ | OCO(4-CF$_3$-3-pyridyl) | 3-pyridyl |
| 271 | OH | OCO—c-C$_3$H$_5$ | OCO—c-C$_3$H$_5$ | OCO(3-Cl-2-pyridyl) | 3-pyridyl |
| 272 | OH | —O—CH(C$_6$H$_5$)—O— | | =O | 3-pyridyl |
| 273 | OH | —O—CH(4-OCH$_3$—C$_6$H$_4$)—O— | | =O | 3-pyridyl |
| 274 | OCO(CH$_2$)$_3$CH$_3$ | —O—CO—O— | | OCO(CH$_2$)$_3$CH$_3$ | 3-pyridyl |
| 275 | OCOCH$_3$ | —O—CH(C$_6$H$_5$)—O— | | OCOCH$_3$ | 3-pyridyl |
| 276 | =O | —O—CH(4-OCH$_3$—C$_6$H$_4$)—O— | | OH | 3-pyridyl |
| 277 | OH | OCO—c-C$_3$H$_5$ | OCO—c-C$_3$H$_5$ | =O | 3-pyridyl |
| 278 | OH | OCO—c-C$_3$H$_5$ | OCO—c-C$_3$H$_5$ | H | 3-pyridyl |
| 279 | OH | OCOCH$_3$ | OCOCH$_3$ | OCOCH$_3$ | 3-pyridyl |

Other pest control agents mixable into the pyripyropene derivatives in the present invention include, for example, fungicides, miticides, herbicides, or plant growth-regulating agents. Specific examples of such agents are described, for example, in The Pesticide Manual, the 13th edition, published by The British Crop Protection Council; and SHIBUYA INDEX, the 10th edition, 2005, published by SHIBUYA INDEX RESEARCH GROUP.

Preferred other pest control agents mixable into the pyripyropene derivatives include insecticide, for example, acephate, dichlorvos, EPN, fenitrothion, fenamifos, prothiofos, profenofos, pyraclofos, chlorpyrifos-methyl, chlorfenvinphos, demeton, ethion, malathion, coumaphos, isoxathion, fenthion, diazinon, thiodicarb, aldicarb, oxamyl, propoxur, carbaryl, fenobucarb, ethiofencarb, fenothiocarb, pirimicarb, carbofuran, carbosulfan, furathiocarb, hyquincarb, alanycarb, methomyl, benfuracarb, cartap, thiocyclam, bensultap, dicofol, tetradifon, acrinathrin, bifenthrin, cycloprothrin, cyfluthrin, dimefluthrin, empenthrin, fenfluthrin, fenpropathrin, imiprothrin, metofluthrin, permethrin, phenothrin, resmethrin, tefluthrin, tetramethrin, tralomethrin, transfluthrin, cypermethrin, deltamethrin, cyhalothrin, fenvalerate, fluvalinate, ethofenprox, flufenprox, halfenprox, silafluofen, cyromazine, diflubenzuron, teflubenzuron, flucycloxuron, flufenoxuron, hexaflumuron, lufenuron, novaluron, penfluoron, triflumuron, chlorfluazuron, diafenthiuron, methoprene, fenoxycarb, pyriproxyfen, halofenozide, tebufenozide, methoxyfenozide, chromafenozide, dicyclanil, buprofezin, hexythiazox, amitraz, chlordimeform, pyridaben, fenpyroxymate, flufenerim, pyrimidifen, tebufenpyrad, tolfenpyrad, fluacrypyrim, acequinocyl, cyflumetofen, flubendiamide, ethiprole, fipronil, ethoxazole, imidacloprid, nitenpyram, clothianidin, acetamiprid, dinotefuran, thiacloprid, thiamethoxam, pymetrozine, bifenazate, spirodiclofen, spiromesifen, flonicamid, chlorfenapyr, pyriproxyfene, indoxacarb, pyridalyl, spinosad, avermectin, milbemycin, azadirachtin, nicotine, rotenone, BT formulations, insect pathological viral agents, emamectinbenzoate, spinetoram, pyrifluquinazon, chiorantraniliprole, cyenopyrafen, spirotetramat, lepimectin, metaflumizone, pyrafluprole, pyriprole, dimefluthrin, fenazaflor, hydramethylnon, triazamate, and compounds of formula (II) described in WO 2006/013896:

[Chemical formula 2]

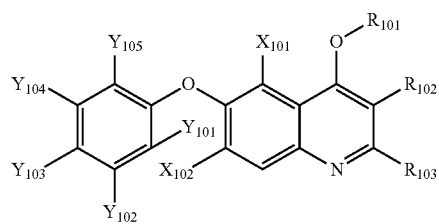

(II)

wherein $R_{101}$ represents $COR_{104}$ or $COOR_{105}$ wherein $R_{104}$ and $R_{105}$ represent $C_{1-4}$ alkyl, preferably $COR_{104}$, $R_{102}$ represents $C_{1-4}$ alkyl, $R_{103}$ represents $C_{1-4}$ alkyl, $X_{101}$ and $X_{102}$ each independently represent a hydrogen atom or $C_{1-4}$ alkyl optionally substituted by a halogen atom, preferably $X_{101}$ represents a hydrogen atom while $X_{102}$ represents $C_{1-4}$ alkyl, provided that $X_{101}$ and $X_{102}$ do not simultaneously represent a hydrogen atom, and $Y_{101}$, $Y_{102}$, $Y_{103}$, $Y_{104}$, and $Y_{105}$ each independently represent a hydrogen atom, $C_{1-8}$ alkyloxy, wherein the $C_{1-8}$ alkyloxy group is substituted by one or more halogen atoms, which may be the same or different, and/or $C_{1-4}$ alkyloxy substituted by one or more halogen atoms, which may be the same or different, or a halogen atom, preferably $Y_{101}$ represents a hydrogen atom or a halogen atom, $Y_{102}$ and $Y_{103}$ represent $C_{1-4}$ alkyloxy substituted by a halogen atom, and $Y_{104}$ and $Y_{ios}$ represent a hydrogen atom, provided that at least one of $Y_{101}$, $Y_{102}$, $Y_{103}$, $Y_{104}$, and $Y_{105}$ represents $C_{1-8}$ alkyloxy, wherein the $C_{1-8}$ alkyloxy group is substituted by one or more halogen atoms, which may be the same or different, and/or $C_{1-4}$ alkyloxy substituted by one or more halogen atoms which may be the same or different, or two adjacent groups of $Y_{101}$, $Y_{102}$, $Y_{103}$, $Y_{104}$, and $Y_{105}$ together may represent —O—$(CH_2)_n$—O—, wherein n is 1 or 2, substituted by one or more halogen atoms.

Examples of further preferred other pest control agents mixable into the pyripyropene derivatives include flonicamid, acetamiprid, fipronil, imidacloprid, chlorfenapyr, clothianidin, thiamethoxam, dinotefuran, and compounds of compound Nos. A120, A190, A257, and A648 included in the compounds of formula (II) wherein $R_{101}$ represents methoxycarbonyl, $R_{102}$ represents methyl, $R_{103}$ represents ethyl, $X_{101}$, $Y_{104}$, and $Y_{105}$ represent a hydrogen atom, $X_{102}$ represents methyl, and $Y_{101}$, $Y_{102}$, and $Y_{103}$ represent a group shown in Table 15 below:

TABLE 15

| Compound No. | $Y_{101}$ | $Y_{102}$ | $Y_{103}$ |
|---|---|---|---|
| A120 | H | H | $OCF_3$ |
| A190 | H | H | $OCF_2CHF_2$ |
| A257 | Cl | H | $OCF_3$ |
| A648 | H | —$OCF_2CF_2O$— | |

Particularly preferred are flonicamid, acetamiprid, fipronil, imidacloprid, and compounds of compound Nos. A120 and A190.

Fungicides mixable into the pyripyropene derivatives include, for example, strobilrin compounds such as azoxystrobin, kresoxym-methyl, trifloxystrobin, orysastrobin, picoxystrobin, and fuoxastrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurase, benalaxyl, furalaxyl, and cyprofuram; sulfenic acid compounds such as dichlofluanid; copper compounds such as copper hydroxide and oxine-copper; isoxazole compounds such as hydroxyisoxazole; organophosphorus compounds such as fosetyl-aluminium and tolclofos-methyl; N-halogenothioalkyl compounds such as captan, captafol, and folpet; dicarboxylmide compounds such as procymidone, iprodione, and vinchlozolin; benzanilide compounds such as flutolanil and mepronil; morpholine comopounds such as fenpropimorph and dimethomorph; organotin compounds such as fenthin hydroxide, and fenthin acetate; and cyanopyrrole compounds such as fludioxonil and fenpiclonil. Other fungicides include fthalide, probenazole, acibenzolar-S-methyl, tiadinil, isotianil, carpropamid, diclocymet, fenoxanil, tricyclazole, pyroquilon, ferimzone, fluazinam, cymoxanil, triforine, pyrifenox, fenarimol, fenpropidin, pencycuron, cyazofamid, cyflufenamid, boscalid, penthiopyrad, proquinazid, quinoxyfen, famoxadone, fenamidone, iprovalicarb, benthiavalicarb-isopropyl, fluopicolide, pyribencarb, kasugamycin, and validamycin.

In another preferred embodiment of the present invention, the pest control composition comprises, as active ingredients, a pyripyropene derivative of formula (I), wherein $Het_1$ represents 3-pyridyl, $R_1$ represents hydroxyl, $R_2$ and $R_3$ represents cyclopropylcarbonyloxy, $R_4$ represents hydroxyl, or an agriculturally and horticulturally acceptable salt thereof and an insecticide as other pest control agent, the insecticide being a compound selected from the group consisting of flonicamid, acetamiprid, fipronil, imidacloprid, chlorfenapyr, clothianidin, thiamethoxam, and dinotefuran and compounds of formula (II) wherein $R_{101}$ represents methoxycarbonyl, $R_{102}$ represents methyl, $R_{103}$ represents ethyl, $X_{101}$, $Y_{104}$, and $Y_{105}$ represent a hydrogen atom, $X_{102}$ represents methyl, and $Y_{101}$, $Y_{102}$, and $Y_{103}$ represent a group shown in Table 16 below:

TABLE 16

| Compound No. | $Y_{101}$ | $Y_{102}$ | $Y_{103}$ |
|---|---|---|---|
| A120 | H | H | $OCF_3$ |
| A190 | H | H | $OCF_2CHF_2$ |
| A257 | Cl | H | $OCF_3$ |
| A648 | H | | —$OCF_2CF_2O$— |

According to another aspect of the present invention, there is provided a pest control composition that, in addition to the above ingredients, comprises a suitable agriculturally and horticulturally acceptable carrier. The pest control composition may be formulated into any suitable dosage forms, for example, emulsifiable concentrates, liquid formulations, suspensions, wettable powders, water dispersible granules, floables, dusts, DL dusts, granules, micro granule fines, tablets, oils, aerosols, smoking agents, or microcapsules. These dosage forms may be produced as described, for example, in "Noyaku Seizai Gaido (Guide for Pesticide Formulation)" edited by "Seyoho Kenkyukai (Special Committee on Agricultural Formulation and Application)", Japan Plant Protection Association, 1997.

Carriers usable herein include solid carriers, liquid carriers, gaseous carriers, surfactants, dispersants, and other adjuvants for formulations.

Solid carriers include, for example, talc, bentonite, clay, kaolin, diatomaceous earth, vermiculite, white carbon, and calcium carbonate.

Liquid carriers include, for example, alcohols such as methanol, n-hexanol, and ethylene glycol; ketones such as acetone, methyl ethyl ketone, and cyclohexanone; aliphatic hydrocarbons such as n-hexane, kerosine, and kerosene; aromatic hydrocarbons such as toluene, xylene, and methylnaphthalene; ethers such as diethyl ether, dioxane, and tetrahydrofuran; esters such as ethyl acetate; nitriles such as acetonitrile and isobutyronitrile; acid amides such as dimethylformamide and dimethylacetamide; vegetable oils such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or spreading include, for example, alkylsulfuric esters, alkyl(aryl)sulfonic acid salts, polyoxyalkylene alkyl(aryl)ethers, polyhydric alcohol esters, and lignin sulfonic acid salts.

Adjuvants usable for improving the properties of formulations include, for example, carboxymethylcellulose, gum arabic, polyethylene glycol, and calcium stearate.

The above carriers, surfactants, dispersants, and adjuvants may be used either solely or in combination according to need.

The total content of the active ingredients in the composition according to the present invention is 0.1 to 99.9% by weight, preferably 0.2 to 80% by weight. The mixing ratio between the pyripyropene derivative of formula (I) and the other pest control agent(s) may vary in a wide range. In general, the composition according to the present invention contains 0.1 to 80% by weight of the pyripyropene derivative.

Pest control compositions, which further comprise agriculturally and horticulturally acceptable carriers, in a preferred embodiment include:

(1) a composition in a wettable powder form comprising 0.1 to 80% by weight of the pyripyropene derivative of formula (I), 0.1 to 80% by weight of an insecticide as the other pest control agent, 0.6 to 30% by weight of a wetting agent and a dispersant, and 20 to 95% by weight of an extender, (2) a composition in a water dispersible granule form comprising 0.1 to 80% by weight of the pyripyropene derivative of formula (I), 0.1 to 80% by weight of an insecticide as the other pest control agent, 0.6 to 30% by weight of a wetting agent, a dispersant, and a binder, and 20 to 95% by weight of an extender, (3) a composition in a floable form comprising 0.1 to 80% by weight of the pyripyropene derivative of formula (I), 0.1 to 80% by weight of an insecticide as the other pest control agent, 5 to 40% by weight of a dispersant, a thickening agent, an antifreezing agent, an antiseptic, and an antifoaming agent, and 20 to 94% by weight of water, (4) a composition in an emulsifiable concentrate comprising 0.1 to 80% by weight of the pyripyropene derivative of formula (I), 0.1 to 80% by weight of an insecticide as the other pest control agent, 1 to 30% by weight of an emulsifier and an emulsion stabilizer, and 20 to 97% by weight of an organic solvent, (5) a composition in a dust form comprising 0.1 to 80% by weight of the pyripyropene derivative of formula (I), 0.1 to 80% by weight of an insecticide as the other pest control agent, and 70 to 99.8% by weight of an extender, (6) a composition in a DL dust (low drift dust) form comprising 0.1 to 80% by weight of the pyripyropene derivative of formula (I), 0.1 to 80% by weight of an insecticide as the other pest control agent, and 70 to 99.8% by weight of an extender, (7) a composition in a micro granule fine form comprising 0.1 to 80% by weight of the pyripyropene derivative of formula (I), 0.1 to 80% by weight of an insecticide as the other pest control agent, 0.2 to 10% by weight of a solvent or a binder, and 70 to 99.6% by weight of an extender, (8) a composition in a granule form comprising 0.1 to 80% by weight of the pyripyropene derivative of formula (I), 0.1 to 80% by weight of an insecticide as the other pest control agent, 0.5 to 30% by weight of a granulation assistant (a surfactant) and a binder, and 20 to 98% by weight of an extender, and (9) a composition in a microcapsule form comprising 0.1 to 80% by weight of the pyripyropene derivative of formula (I), 0.1 to 80% by weight of an insecticide as the other pest control agent, 1 to 50% by weight of a coating agent, an emulsifier, a dispersant, and an antiseptic, and 20 to 98% by weight of water. Among them, the composition (1), (2), (3), (4), (7), or (8) is preferred, and the composition (2), (3), (4), or (8) is more preferred.

In the pest control composition according to the present invention, a method may be adopted in which a first composition containing, as active ingredient, only a first active ingredient of the pest control composition according to the present invention, i.e., at least one pyripyropene derivative of formula (I) or agriculturally and horticulturally acceptable salt thereof, and a second composition containing, as active ingredient, only a second active ingredient of the pest control composition according to the present invention, i.e., at least one other pest control agent, are prepared and, in use, these two compositions are mixed together on site.

Thus, according to still another aspect of the present invention, there is provided a combination comprising at least one pyripyropene derivative of formula (I) or agriculturally and horticulturally acceptable salt thereof and at least one other pest control agent.

In another preferred embodiment of the present invention, in the combination, the at least one pyripyropene derivative of formula (I) or agriculturally and horticulturally acceptable salt thereof is provided as a first composition containing the at least one pyripyropene derivative of formula (I) or agriculturally and horticulturally acceptable salt thereof as active ingredient, and at least one other pest control agent is provided as a second composition containing the at least one other pest control agent as active ingredient. In this case, as with the above pest control composition, the first and second compositions may be in any desired dosage form using a suitable carrier or adjuvant. The combination may also be provided in a form like a drug set.

According to a further aspect of the present invention, there is provided a method protecting useful plants from pests, comprising applying at least one pyripyropene derivative of formula (I) or agriculturally and horticulturally acceptable salt thereof and at least one other pest control agent simultaneously or separately from each other to an area to be treated.

In this method, applying "simultaneously" embraces a case where at least one pyripyropene derivative of formula (I) or agriculturally and horticulturally acceptable salt thereof and at least one other pest control agent are mixed together before application to an area to be treated and the mixture is applied to the object area. On the other hand, applying "separately" embraces a case where, without previously mixing at least one pyripyropene derivative of formula (I) or agriculturally and horticulturally acceptable salt thereof and at least one other pest control agent together, at least one pyripyropene derivative of formula (I) or agriculturally and horticulturally acceptable salt thereof is applied before the application of at least one other pest control agent, and a case where, without previously mixing at least one pyripyropene derivative of formula (I) or agriculturally and horticulturally acceptable salt thereof and at least one other pest control agent together, at least one pyripyropene derivative of formula (I) or agriculturally and horticulturally acceptable salt thereof is applied after the application of at least one other pest control agent.

According to another aspect of the present invention, there is provided a method for protecting useful plants from pests, comprising applying (1) a first composition comprising at least one pyripyropene derivative of formula (I) or agriculturally and horticulturally acceptable salt thereof as active ingredient and (2) a second composition comprising at least one other pest control agent as active ingredient to an area to be treated.

According to still another aspect of the present invention, there is provided a method for protecting useful plants from pests, comprising treating an object pest, an object useful plant, or a seed, a soil, or a cultivation carrier of the object useful plant with the pest control composition or the combination according to the present invention as such or after dilution.

According to a further aspect of the present invention, there is provided use of the pest control composition or the combination according to the present invention for the protection of useful plants from pests.

Methods for treating the object pest, the object useful plant, or the seed, soil, or cultivation carrier of the object useful plant with the pest control composition according to the present invention include, for example, spreading treatment, soil treatment, surface treatment, and fumigation. Spreading treatments include, for example, spreading, spraying, misting, atomizing, granule, application, and application to water surface. Soil treatments include, for example, soil drenching and soil admixing. Surface treatments include, for example, coating, dressing, and covering. Fumigation treatments include, for example, covering of soil with a polyethylene film after soil injection. Accordingly, the use of the pest control composition according to the present invention includes the application of the pest control composition according to the present invention by fumigation in a sealed space.

Insect pest species against which the composition according to the present invention exhibits control effect include: lepidopteran insect pests, for example, *Spodoptera litura*, *Mamestra brassicae*, *Pseudaletia separata*, green caterpillar, *Plutella xylostella*, *Spodoptera exigua*, *Chilo suppressalis*, *Cnaphalocrocis medinalis*, Tortricidae, Carposimidae, Lyonetiidae, Lymantriidae, insect pests belonging to the genus *Agrotis* spp., insect pests belonging to the genus *Helicoverpa* spp., and insect pests belonging to the genus *Heliothis* spp.; hemipteran insect pests, for example, Aphididae, Adelgidae or Phylloxeridae such as *Myzus persicae*, *Aphis gossypii*, *Aphis fabae*, *Aphis maidis* (corn-leaf aphid), *Acyrthosiphon pisum*, *Aulacorthum solani*, *Aphis craccivora*, *Macrosiphum euphorbiae*, *Macrosiphum avenae*, *Methopolophium dirhodum*, *Rhopalosiphum padi*, *Schizaphis graminum*, *Brevicoryne brassicae*, *Lipaphis erysimi*, *Aphis citricola*, Rosy apple aphid, *Eriosoma lanigerum*, *Toxoptera aurantii*, and *Toxoptera citricidus*, Deltocephalidae such as *Nephotettix cincticeps*, Delphacidae such as *Laodelphax striatellus*, *Nilaparvata lugens*, and *Sogatella furcifera*, Pentatomidae such as *Eysarcoris ventralis*, *Nezara viridula*, and *Trigonotylus ruficornis*, Aleyrodidae such as *Bemisia tabaci* Genn., *Bemisia tabaci*, and *Trialeurodes vaporariorum*, and Diaspididae, Margarodidae, Ortheziidae, Aclerdiae, Dactylopiidae, Kerridae, Pseudococcidae, Coccidae, Eriococcidae, Asterolecamidae, Beesonidae, Lecanodiaspididae, or Cerococcidae, such as *Pseudococcus comstocki* and *Planococcus citri Risso*; Coleoptera insect pests, for example, *Lissorhoptrus oryzophilus*, *Callosobruchuys chienensis*, *Tenebrio molitor*, *Diabrotica virgifera virgifera*, *Diabrotica undecimpunctata howardi*, *Anomala cuprea*, *Anomala rufocuprea*, *Phyllotreta striolata*, *Aulacophora femoralis*, *Leptinotarsa decemlineata*, *Oulema oryzae*, Bostrychidae, and Cerambycidae; Acari, for example, *Tetranychus urticae*, *Tetranychus kanzawai*, and *Panonychus citri*; Hymenopteran insect pests, for example, Tenthredimidae; Orthopteran insect pests, for example, Acrididae; Dipteran insect pests, for example, Muscidae and Agromyzidae; Thysanopteran insect pests, for example, *Thrips palmi* and *Frankliniella occidentalis*; Plant Parasitic Nematodes, for example, *Meloidogyne hapla*, *Pratylenchus*, *Aphelenchoides besseyi*, and *Bursaphelenchus xylophilus*; and zooparasite, for example, Aphaniptera, Anoplura, mites such as *Boophilus* spp., *Haemaphysalis longicornis*, *Rhipicephalus sanguineus*, and *Sarcoptes* spp. Preferred are hemipteran insect pests and lepidopteran insect pests.

Preferred hemipteran insect pests are selected from Aphididae, Adelgidae, and Phylloxeridae, particularly preferably Aphididae; Diaspididae, Margarodidae, Ortheziidae, Aclerdiae, Dactylopiidae, Kerridae, Pseudococcidae, Coccidae, Eriococcidae, Asterolecamidae, Beesonidae, Lecanodiaspididae, and Cerococcidae; or Aleyrodidae. More preferred are *Myzus persicae*, *Aphis gossypii*, *Aphis fabae*, *Aphis maidis* (corn-leaf aphid), *Acyrthosiphon pisum*, *Aulacorthum solani*, *Aphis craccivora*, *Macrosiphum euphorbiae*, *Macrosiphum avenae*, *Metopolophium dirhodum*, *Rhopalosiphum padi*, *Schizaphis graminum*, *Brevicoryne brassicae*, *Lipaphis erysimi*, *Aphis citricola*, Rosy apple aphid, *Erio-* soma lanigerum, Toxoptera aurantii, Toxoptera citricidus, Pseudococcus comstocki, or Trialeurodes vaporariorum (Greenhouse whitefly).

EXAMPLES

The present invention is further illustrated by the following Examples that are not intended as a limitation of the invention. In the Examples, compounds 261 and 237 were synthesized as described in WO 2006/129714, and compounds A120, A190, A257, and A648 were synthesized as described in WO 2006/013896.

Synthetic Examples

Synthetic Example 1 (Synthetic Example of Compound 277)

Compound 261 (20 mg) was dissolved in dichloromethane (1 ml). Dess-Martin periodinane (21 mg) was added to the solution at 0° C., and, in this state, the mixture was stirred for 2 hr 40 min. A saturated aqueous sodium thiosulfate solution was added to the reaction solution, and the mixture was extracted with chloroform. The chloroform layer was washed with saturated brine and was dried over anhydrous magnesium sulfate. The solvent was then removed by evaporation under the reduced pressure, and the crude product thus obtained was purified by preparative thin-layer chromatography (Merck silica gel 60 F (0.5 mm), acetone:hexane=1:1) to give compound 277 (5.4 mg).

Synthetic Example 2 (Synthetic Example of Compound 278)

Compound 261 (50 mg) was dissolved in toluene (3 ml). 1,1'-Thiocarbonyldiimidazole (90 mg) was added to the solution at room temperature, and the mixture was heated under reflux for 2.5 hr. The reaction solution was cooled to room temperature. Water was added to the reaction solution, and the mixture was extracted with ethyl acetate. The ethyl acetate layer was washed with saturated brine and was dried over anhydrous magnesium sulfate, and the solvent was then removed by evaporation under the reduced pressure. The crude product thus obtained was purified by preparative thin-layer chromatography (Merck silica gel 60 F (0.5 mm), acetone:hexane=1:1). The product (41 mg) thus obtained was dissolved in toluene (2 ml), tri-n-butyltin hydride (20 mg) was added to the solution at room temperature, and the mixture was heated under reflux for 2.5 hr. The reaction solution was cooled to room temperature, water was added to the cooled reaction solution, and the mixture was extracted with ethyl acetate. The ethyl acetate layer was washed with saturated brine and was dried over anhydrous magnesium sulfate, and the solvent was then removed by evaporation under the reduced pressure. The crude product thus obtained was purified by preparative thin-layer chromatography (Merck silica gel 60 F (0.5 mm), acetone:hexane=1:1) to give compound 278 (3.5 mg).

For compounds 227 and 278 produced in Synthetic Examples 1 and 2, $^1$H-NMR data and mass spectrometric data are shown in Table 17.

TABLE 17

| Compound | Solvent | NMR data $^1$H-NMR δ (ppm) | Mass spectrometric data Measuring method | Data |
|---|---|---|---|---|
| 277 | CDCl$_3$ | 0.83-1.00 (8H, m), 0.96 (3H, s), 1.44 (1H, m), 1.53-1.61 (2H, m), 1.63 (3H, s), 1.76 (1H, d, J = 3.7 Hz), 1.81 (3H, s), 1.87 (2H, m), 1.94-1.97 (1H, m), 2.21 (1H, m), 2.53 (1H, dd, J = 2.6, 14.9 Hz), 2.78 (1H, t, J = 14.9 Hz), 2.91 (1H, d, J = 1.5 Hz), 3.66 (1H, d, J = 12.0 Hz), 3.84 (1H, d, J = 12.0 Hz), 4.82 (1H, dd, J = 4.8, 11.7 Hz), 5.06 (1H, m), 6.71 (1H, s), 7.41 (1H, dd, J = 4.8, 8.0 Hz), 8.09 (1H, dt, J = 1.7, 8.0 Hz), 8.70 (1H, dd, J = 1.7, 4.8 Hz), 9.02 (1H, d, J =1.7 Hz) | ESI | 592 (M + H)$^+$ |
| 278 | CDCl$_3$ | 0.84-1.00 (8H, m), 0.90 (3H, s), 1.12-1.16 (1H, m), 1.25 (1H, s), 1.35-1.46 (1H, m), 1.41 (3H, s), 1.56-1.70 (5H, m), 1.66 (3H, s), 1.78-1.89 (2H, m), 2.12-2.17 (2H, m), 2.82 (1H, d, J = 1.4 Hz), 3.69 (1H, d, J = 11.9 Hz), 3.91 (1H, d, J = 11.9 Hz), 4.83 (1H, dd, J = 5.1, 11.5 Hz), 4.99 (1H, m), 6.46 (1H, s), 7.42 (1H, m), 8.11 (1H, dt, J = 1.7, 8.0 Hz), 8.69 (1H, m), 9.01 (1H, m) | ESI | 578 (M + H)$^+$ |

Preparation Examples

Preparation Example 1 [Wettable Powder]

| | |
|---|---|
| Pyripyropene derivative (compound 261) | 10 wt % |
| Imidacloprid | 20 wt % |
| Clay | 50 wt % |
| White carbon | 2 wt % |
| Diatomaceous earth | 13 wt % |
| Calcium lignin sulfonate | 4 wt % |
| Sodium lauryl sulfate | 1 wt % |

The above ingredients were intimately mixed together, and the mixture was ground to prepare wettable powder.

Preparation Example 2 [Water Dispersible Granule]

| | |
|---|---|
| Pyripyropene derivative (compound 237) | 10 wt % |
| Imidacloprid | 20 wt % |
| Clay | 60 wt % |
| Dextrin | 5 wt % |
| Alkylmaleic acid copolymer | 4 wt % |
| Sodium lauryl sulfate | 1 wt % |

The above ingredients were homogeneously ground and intimately mixed together. Water was added to the mixture, followed by thorough kneading. Thereafter, the kneaded product was granulated and dried to prepare a water dispersible granule.

Preparation Example 3 [Floables]

| | |
|---|---|
| Pyripyropene derivative (compound 261) | 5 wt % |
| Flonicamid | 20 wt % |
| POE polystyryl phenyl ether sulfate | 5 wt % |
| Propylene glycol | 6 wt % |
| Bentonite | 1 wt % |
| 1% aqueous xanthan gum solution | 3 wt % |
| PRONAL EX-300 (Toho Chemical Industry Co., Ltd.) | 0.05 wt % |
| ADDAC 827 (K.I. Chemical Industry Co., Ltd.) | 0.02 wt % |
| Water | To 100 wt % |

All the above ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100 wt % floables.

Preparation Example 4 [Emulsifiable Concentrate]

| | |
|---|---|
| Pyripyropene derivative (compound 237) | 2 wt % |
| Acetamiprid | 13 wt % |
| N,N-dimethylformamide | 20 wt % |
| Solvesso 150 (Exxon Mobil Corporation) | 55 wt % |
| Polyoxyethylene alkyl aryl ether | 10 wt % |

The above ingredients were intimately mixed together and dissolved to prepare an emulsifiable concentrate.

Preparation Example 5 [Dust]

| | |
|---|---|
| Pyripyropene derivative (compound 277) | 0.5 wt % |
| Acetamiprid | 1.5 wt % |
| Clay | 60 wt % |
| Talc | 37 wt % |
| Calcium stearate | 1 wt % |

The above ingredients were intimately mixed together to prepare dust.

Preparation Example 6 [DL Dust]

| | |
|---|---|
| Pyripyropene derivative (compound 277) | 1 wt % |
| Fipronil | 1 wt % |
| DL clay | 94.5 wt % |
| White carbon | 2 wt % |
| Calcium stearate | 1 wt % |
| Light liquid paraffin | 0.5 wt % |

The above ingredients were intimately mixed together to prepare DL dust.

Preparation Example 7 [Micro Granule Fine]

| | |
|---|---|
| Pyripyropene derivative (compound 261) | 1 wt % |
| Flonicamid | 1 wt % |
| Carrier | 94 wt % |
| White carbon | 2 wt % |
| Hisol SAS-296 | 2 wt % |

The above ingredients were intimately mixed together to prepare micro granule fine.

Preparation Example 8 [Granules]

| | |
|---|---|
| Pyripyropene derivative (compound 278) | 2 wt % |
| Flonicamid | 3 wt % |
| Bentonite | 40 wt % |
| Talc | 10 wt % |
| Clay | 43 wt % |
| Calcium lignin sulfonate | 2 wt % |

The above ingredients were homogeneously ground and intimately mixed together. Water was added to the mixture, followed by thorough kneading. Thereafter, the kneaded product was granulated and dried to prepare granules.

Preparation Example 9 [Microcapsules]

| | |
|---|---|
| Pyripyropene derivative (compound 237) | 2 wt % |
| Imidacloprid | 3 wt % |
| Urethane resin | 25 wt % |
| Emulsifying dispersant | 5 wt % |
| Antiseptic | 0.2 wt % |
| Water | 64.8 wt % |

The above ingredients were polymerized by interfacial polymerization to form a urethane resin film on the surface of pyripyropene derivative particles and imidacloprid particles and thus prepare microcapsules.

Test Examples

Test Example 1: Pesticidal Effect Against *Aphis gossypii* (Part 1)

A leaf disk having a diameter of 2.0 cmφ was cut out from a cucumber grown in a pot and was placed in a 5.0 cm-Schale. Test admixture solutions, prepared by diluting the composition of the present invention with a 50% aqueous acetone solution (0.05% Tween 20 added) to predetermined concentrations specified in Table 18, test single active ingredient solutions in which only compound 261 had been dissolved without mixing other insecticides, or test single active ingredient solutions in which only other insecticides had been dissolved without mixing any pyripyropene derivative were spread over the cucumber leaf disk. The leaf disk was then air dried. Ten larvae at the first instar born of *Aphis gossypii* were released in the Schale. Thereafter, the Schale was lidded and was allowed to stand in a humidistat chamber (light period 16 hr-dark period 8 hr) (25° C.). Three days after the initiation of standing of the Schale, the larvae were observed for survival or death, and the death rate of larvae was calculated by the following equation. The results are shown in Table 18.

Death rate (%)={number of dead larvae/(number of survived larvae+number of dead larvae)}×100

Further, theoretical values, which do not exhibit a synergistic effect, were calculated by the following Colby's formula, and the results are shown in Table 19.

Colby's formula: Theoretical value (%)=100−(A×B)/100 wherein A: 100—(death rate when treatment was performed only with compound 261); and B: 100—(death rate when treatment was performed only with each of flonicamid, acetamiprid, fipronil, imidacloprid)

Method for Determining Synergistic Effect

When the pesticidal effect (Table 18) of the composition of the present invention in, an admixture form against *Aphis gossypii* exceeded the theoretical value calculated by the Colby's formula shown in Table 19, the admixture was determined to have a synergistic effect.

All the tested admixtures had the death rate beyond the theoretical values, demonstrating that they had a synergistic effect.

TABLE 18

Death rate of *Aphis gossypii* by single active ingredient or admixture (%)

| Other insecticides | | Compound 261 | |
|---|---|---|---|
| | | 0 ppm | 0.01 ppm |
| — | | 0 | 30 |
| Flonicamid | 0.078 ppm | 10 | 60 |
| Acetamiprid | 0.078 ppm | 58 | 100 |
| Fipronil | 0.078 ppm | 0 | 63 |
| Imidacloprid | 0.078 ppm | 20 | 95 |

TABLE 19

Theoretical value calculated by Colby's formula (%)

| Other insecticides | | Compound 261 | |
|---|---|---|---|
| | | 0 ppm | 0.01 ppm |
| — | | 0 | 30 |
| Flonicamid | 0.078 ppm | 10 | 37 |
| Acetamiprid | 0.078 ppm | 58 | 71 |
| Fipronil | 0.078 ppm | 0 | 30 |
| Imidacloprid | 0.078 ppm | 20 | 44 |

Test Example 2: Pesticidal Effect Against *Aphis gossypii* (Part 2)

The same test as in Test Example 1 was performed, except that the other insecticides were changed to those specified in Table 20. The pesticidal effect and theoretical values were calculated, and the results are shown in Tables 20 and 21.

All the tested admixtures had the death rate beyond the theoretical values, demonstrating that they had a synergistic effect.

TABLE 20

Pesticidal effect against *Aphis gossypii*, death rate (%)

| Other insecticides | | Compound 261 | |
|---|---|---|---|
| | | 0 ppm | 0.01 ppm |
| — | | 0 | 53 |
| Clothianidin | 0.078 ppm | 79 | 100 |
| Thiamethoxam | 0.078 ppm | 65 | 90 |
| Dinotefuran | 0.078 ppm | 40 | 75 |

TABLE 21

Theoretical value calculated by Colby's formula (%)

| Other insecticides | | Compound 261 | |
|---|---|---|---|
| | | 0 ppm | 0.01 ppm |
| — | | 0 | 53 |
| Clothianidin | 0.078 ppm | 79 | 90 |
| Thiamethoxam | 0.078 ppm | 65 | 84 |
| Dinotefuran | 0.078 ppm | 40 | 72 |

Test Example 3: Pesticidal Effect Against *Plutella xylostella*

A leaf disk having a diameter of 5.0 cmφ was cut out from a cabbage grown in a pot and was placed in a plastic cup. Test admixture solutions, prepared by diluting the composition of the present invention with a 50% aqueous acetone solution (0.05% Tween 20 added) to predetermined concentrations specified in Table 22, test single active ingredient solutions in which only compound 261 had been dissolved without mixing other insecticides, or test single active ingredient solutions in which only other insecticides had been dissolved without mixing any pyripyropene derivative were spread over the cabbage leaf disk. The leaf disk was then air dried. Five larvae at the second instar born of *Plutella xylostella* were released in the cup. Thereafter, the cup was lidded and was allowed to stand in a humidistat chamber (light period 16 hr-dark period 8 hr) (25° C.). Three days after the initiation of standing of the cup, the larvae were observed for survival or death, and the death rate of larvae was calculated by the following equation. The results are shown in Table 22.

Death rate (%)={number of dead larvae/(number of survived larvae+number of dead larvae)}×100

The death rates are shown below.

Further, theoretical values, which do not exhibit a synergistic effect, were calculated by the following Colby's formula, and the results are shown in Table 23.

Colby's formula: Theoretical value (%)=100−(A×B)/100 wherein A: 100—(death rate when treatment was performed only with compound 261); and B: 100—(death rate when treatment was performed only with each compound, i.e., A120, A190, or chlorfenapyr)

Method for Determining Synergistic Effect

When the pesticidal effect (Table 22) of the composition of the present invention in an admixture form against *Plutella xylostella* exceeded the theoretical value calculated by the Colby's formula shown in Table 23, the admixture was determined to have a synergistic effect.

All the tested admixtures had the death rate beyond the theoretical values, demonstrating that they had a synergistic effect.

TABLE 22

Pesticidal effect against *Plutella xylostella*, deathrate (%)

| Other insecticides | | Compound 261 | |
|---|---|---|---|
| | | 0 ppm | 10 ppm |
| — | | 0 | 0 |
| Compound A120 (WO2006/013896) | 0.156 ppm | 10 | 50 |
| Compound A190 (WO2006/013896) | 0.313 ppm | 0 | 20 |
| Chlorfenapyr | 0.156 ppm | 0 | 20 |

TABLE 23

Theoretical value calculated by Colby's formula (%)

| Other insecticides | | Compound 261 | |
|---|---|---|---|
| | | 0 ppm | 10 ppm |
| — | | 0 | 0 |
| Compound A120 (WO2006/013896) | 0.156 ppm | 10 | 10 |
| Compound A190 (WO2006/013896) | 0.313 ppm | 0 | 0 |
| Chlorfenapyr | 0.156 ppm | 0 | 0 |

The invention claimed is:

1. A pest control composition comprising at least one pyripyropene derivative of chemical formula (I) or agriculturally and horticulturally acceptable salt thereof and at least one other pest control agent selected from the group consisting of flonicamid, fipronil, chlorfenapyr, clothianidin, thiamethoxam, and dinotefuran as active ingredients:

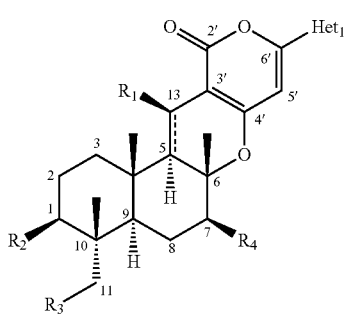

(I)

wherein
$Het_1$ represents 3-pyridyl,
$R_1$ represents hydroxyl,
$R_2$ and $R_3$ represent cyclopropylcarbonyloxy, and
$R_4$ represents hydroxyl, and
wherein the pest control composition comprises 11 to 80% by weight of the at least one pyripyropene derivative of chemical formula (I) or agriculturally and horticulturally acceptable salt thereof and 2 to 80% by weight of the at least one other pest control agent based on the weight of the pest control active ingredients.

2. The composition according to claim 1, which further comprises an agriculturally and horticulturally acceptable carrier.

3. The composition according to claim 1, which is a wettable powder comprising 11 to 80% by weight of the pyripyropene derivative of formula (I), 2 to 80% by weight of the other pest control agent, based on the weight of the pest control active ingredients, 0.6 to 30% by weight of a wetting agent and a dispersant, and 20 to 95% by weight of an extender.

4. The composition according to claim 1, which is a water dispersible granule comprising 11 to 80% by weight of the pyripyropene derivative of formula (I) 2 to 80% by weight of the other pest control agent, based on the weight of the pest control active ingredients, 0.6 to 30% by weight of a wetting agent, a dispersant, and a binder, and 20 to 95% by weight of an extender.

5. The composition according to claim 1, which is a floable preparation comprising 11 to 80% by weight of the pyripyropene derivative of formula (I), 2 to 80% by weight of the other pest control agent, based on the weight of the pest control active ingredients, 5 to 40% by weight of a dispersant, a thickening agent, an antifreezing agent, an antiseptic, and an antifoaming agent, and 20 to 94% by weight of water.

6. The composition according to claim 1, which is an emulsifiable concentrate comprising 11 to 80% by weight of the pyripyropene derivative of formula (I), 2 to 80% by weight of the other pest control agent, based on the weight of the pest control active ingredients, 1 to 30% by weight of an emulsifier and an emulsion stabilizer, and 20 to 97% by weight of an organic solvent.

7. The composition according to claim 1, which is a micro granule fine comprising 11 to 80% by weight of the pyripyropene derivative of formula (I), 2 to 80% by weight of the other pest control agent, based on the weight of the pest control active ingredients, 0.2 to 10% by weight of a solvent or a binder, and 70 to 99.6% by weight of an extender.

8. The composition according to claim 1, which is a granule comprising 11 to 80% by weight of the pyripyropene derivative of formula (I), 2 to 80% by weight of the other pest control agent, based on the weight of the pest control active ingredients, 0.5 to 30% by weight of a granulation assistant (a surfactant) and a binder, and 20 to 98% by weight of an extender.

9. A method for protecting useful plants from pests, comprising applying the pest control composition according to claim 1 to an area to be treated.

10. The method according to claim 9, wherein the ingredients are simultaneously applied to the area to be treated.

11. A method for protecting useful plants from pests, comprising treating an object pest, an object useful plant, or a seed, a soil, or a cultivation carrier of the object useful plant with the pest control composition according to claim 1.

* * * * *